(12) United States Patent
Yan et al.

(10) Patent No.: US 9,757,429 B2
(45) Date of Patent: *Sep. 12, 2017

(54) METHODS FOR DETECTING CARDIAC DAMAGE

(71) Applicant: Acorda Therapeutics, Inc., Ardsley, NY (US)

(72) Inventors: Xinhua Yan, Boston, MA (US); Anthony O. Caggiano, Larchmont, NY (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/053,284

(22) Filed: Feb. 25, 2016

(65) Prior Publication Data

US 2016/0263192 A1 Sep. 15, 2016

Related U.S. Application Data

(63) Continuation of application No. 14/153,695, filed on Jan. 13, 2014, now Pat. No. 9,329,171, which is a continuation of application No. 12/451,397, filed as application No. PCT/US2008/006060 on May 12, 2008, now Pat. No. 8,628,929.

(60) Provisional application No. 60/928,541, filed on May 10, 2007.

(51) Int. Cl.
| | |
|---|---|
| *G01N 33/53* | (2006.01) |
| *A61K 38/18* | (2006.01) |
| *G01N 33/50* | (2006.01) |
| *G01N 33/68* | (2006.01) |
| *A61K 49/00* | (2006.01) |

(52) U.S. Cl.
CPC ...... *A61K 38/1883* (2013.01); *A61K 49/0004* (2013.01); *G01N 33/5061* (2013.01); *G01N 33/5091* (2013.01); *G01N 33/6887* (2013.01); *G01N 2333/47* (2013.01); *G01N 2333/4712* (2013.01); *G01N 2800/32* (2013.01); *G01N 2800/324* (2013.01)

(58) Field of Classification Search
None
See application file for complete search history.

(56) References Cited

U.S. PATENT DOCUMENTS

| | | | |
|---|---|---|---|
| 5,324,502 A | 6/1994 | Green et al. | |
| 5,530,109 A | 6/1996 | Goodearl et al. | |
| 6,635,249 B1 | 10/2003 | Marchionni et al. | |
| 7,776,817 B2 | 8/2010 | Ford | |
| 7,973,007 B2 | 7/2011 | Ford | |
| 2006/0019888 A1 | 1/2006 | Zhou | |

FOREIGN PATENT DOCUMENTS

| | | |
|---|---|---|
| CN | 1584143 A | 2/2005 |
| CN | 1655804 A | 8/2005 |
| CN | 1715926 A | 1/2006 |
| JP | 2002510247 A | 4/2002 |
| JP | 2002542270 A | 12/2002 |
| JP | 2005532332 A | 10/2005 |
| WO | WO-9426298 A1 | 11/1994 |
| WO | WO-0064400 A2 | 11/2000 |
| WO | WO-03099300 A1 | 12/2003 |
| WO | WO-2012021818 A2 | 2/2012 |

OTHER PUBLICATIONS

Adamcova et al. "In vitro and in vivo Examination of Cardiac Troponins as Biochemical Markers of Drug-Induced Cardiotoxicity." Toxicol. 38.23(2007):218-228.
Australian Examination Report issued Jul. 3, 2013 in corresponding AU Application No. 2008251822.
Australian Examination Report issued Mar. 5, 2015 in corresponding AU Application No. 2014202390.
Australian Examination Report issued Sep. 26, 2012 in corresponding AU Application No. 2008251822.
Bertinchant et al. "Evaluation of Cardiac Troponin I and T Levels as Markers of Myocardial Damage in Doxorubicin-Induced Cardiomyopathy Rats, and Their Relationship With Echocardiographic and Histological Findings." Clin. Chim. Acta. 329.1-2(2003):39-51.
Bertinchant et al. "Release Kinetics of Serum Cardiac Troponin I in Ischemic Myocardial Injury." Clin. Biochem. 29.6(1996):587-594.
Bian et al. "Neuregulin-1 Attenuated Doxorubicin-Induced Decrease in Cardiac Troponins." Am. J. Physiol. Heart Circ. Physiol. 297.6(2009):H1974-H1983.
Birks et al. "Gene Profiling Changes in Cytoskeletal Proteins During Clinical Recovery After Left Ventricular-Assist Device Support." Circ. 223.S9(2005):157-164.
Bublil et al. "The EGF Receptor Family: Spearheading a Merger of Signaling and Therapeutics." Curr. Opin. Cell Biol. 19.2(2007):124-134.
Buchwald et al. "Long-Term, Continuous Intravenous Heparin Administration by an Implantable Infusion Pump in Ambulatory Patients With Recurrent Venous Thrombosis." Surgery. 88.4(1980):507-516.
Buonanno et al. "Neuregulin and ErbB Receptor Signaling Pathways in the Nervous System." Curr. Opin. Neurobiol. 11.3(2001):287-296.

(Continued)

*Primary Examiner* — Jacob Cheu
(74) *Attorney, Agent, or Firm* — Mintz Levin Cohn Ferris Glovsky and Popeo, P.C.

(57) ABSTRACT

The present invention relates to a method for detecting heart damage in a patient. The invention also relates to methods for treatment of patients identified as having heart damage. The invention further pertains to methods for evaluating the efficacy of an ongoing therapeutic regimen designated to treat a damaged heart in a patient.

11 Claims, 20 Drawing Sheets

(56) References Cited

OTHER PUBLICATIONS

Campbell et al. "Cardioprotective Effects of a Novel Proteasome Inhibitor Following Ischemia Repefusion in the Isolated Perfused Rat Heart." J. Mol. Cell. Cardiol. 31.2(1999):467-476.
Canadian Office Action issued Nov. 25, 2015 in corresponding CA Application No. 2686959.
Canadian Office Action issued Oct. 30, 2014 in corresponding CA Application No. 2686959.
Cannella et al. "The Neuregulin, Glial Growth Factor 1, Diminishes Autoimmune Demyelination and Enhances Remyelination in a Chronic Relapsing Modle for Multiple Sclerosis." PNAS. 95.17(1998)1 0100-10105.
Chen et al. "Molecular and Cellular Mechanisms of Anthracycline Cardiotoxicity." Cardiovasc. Toxicol. 7(2007):114-121.
Chinese Office Action issued Apr. 24, 2013 in corresponding CN Application No. 200880021887.5.
Chinese Office Action issued Dec. 28, 2015 in corresponding CN Application No. 201410827283.7.
Chinese Office Action issued Dec. 6, 2013 in corresponding CN Application No. 200880021887.5.
Chinese Office Action issued Jun. 20, 2012 in corresponding CN Application No. 200880021887.5.
Chinese Office Action issued May 5, 2014 in corresponding CN Application No. 200880021887.5.
Chinese Office Action issued Sep. 28, 2014 in corresponding CN Application No. 200880021887.5.
Day et al. "Genetic Engineering and Therapy for Inherited and Acquired Cardiomyopathies." Ann. N. Y. Acad. Sci. 1080(2006):437-450.
Day et al. "Tuning Cardiac Performance in Ischemic Heart Disease and Failure by Modulating Myofilament Function." J. Mol. Med. 85(2007):911-921.
De Jonge et al. "Similar Left and Right Ventriular Sarcomere Structure After Support With a Left Ventricular Assistn Device Suggesting the Utility of Right Ventricular Biopsies to Monitor Left Ventricular Reverse Remodeling." Int. J. Cardiol. 98(2005):465-470.
During et al. "Controlled Release of Dopamine From a Polymeric Brain Implant: In Vivo Characterization." Ann. NeuroL 25.4(1989):351-356.
Elliott et al. (J. Mol. Med. 2003 vol. 81, p. 235-245).
Etievent. "Use of Cardiac Troponin I as a Marker of Perioperative Myocardial Ischemia." Ann. Thorac. Surg. 59.5(1995):1192-1194.
European Office Communication for European Patent Application No. 08767674.8, issued Mar. 24, 2011.
European Search Report Issued Jul. 5, 2010 in corresponding EP Application No. 08767674.8.
Evdokimov. "Clinical Picture." *Prehospital Diagnosis and Treatment of Heart Injuries*. Guidelines No. 38(2005):13-14. (English Translation).
Falls. "Neuregulins: Functions, Forms, and Signaling Strategies." Exp. Cell Res. 284.1(2003):14-30.
Fukazawa et al. "Neuregulin-1 Protects Ventricular Myocytes From Anthracycline-Induced Apoptosis via erbB4-Dependent Activation of P13-Kinase/Akt." J. Mol. Cell Cardiol. 35.12(2003):1473-1479.
Gassmann et al. "Aberrant Neural and Cardiac Development in Mice Lacking the ErbB4 Neuregulin Receptor." Nature. 378.6555(1995):390-394.
Goodson. "Dental Applications." *Medical Applications of Controlled Release*. Langer et al., eds. Boca Raton, FL: CRC Press, Inc. 2(1984):115-138.
Greenbaum et al. "Comparing Protein Abundance and mRNA Expression Levels on a Genomic Scale." Genome Biol. 4(2003):117.
Herman et al. "Use of Cardiac Troponin T Levels as an Indicator of Doxorubicin-Induced Cardiotoxicity." Cancer Res. 58.2(1998):195-197.
Howard et al. "Intracerebral Drug Delivery in Rats With Lesion-Induced Memory Deficits." J. Neurosurg. 71.1(1989):105-112.
Hynes et al. "ErbB Receptors and Signaling Pathways in Cancer." Curr. Opin. Cell Biol. 21.2(2009):177-184.
Iaci et al. "Glial Growth Factor 2 Promotes Functional Recovery With Treatment Initiated Up to 7 Days After Permanent Focal Ischemic Stroke." Neuropharmacol. 59.7-8(2010):640-649.
Indian Office Action issued Jun. 17, 2013 in corresponding in Application No. 2094/MUMNP/2009.
International Preliminary Report on Patentability, issued Nov. 10, 2009 in corresponding PCT Application No. PCT/US2008/006060.
International Search Report, issued Jul. 15, 2008 in corresponding PCT Application No. PCT/US2008/006060.
Ito et al. "Doxorubicin Selectively Inhibits Muscle Gene Expression in Cardiac Muscle Cells in vivo and in vitro." PNAS. 87.11(1990):4275-4279.
Japanese Office Action issued Mar. 16, 2015 in corresponding JP Application No. 2014-071111.
Japanese Office Action issued Oct. 30, 2015 in corresponding JP Application No. 2014-071111.
Japanese Office Action issued Sep. 19, 2014 in corresponding JP Application No. 2010-507486.
Japanese Office Action issued Sep. 25, 2013 in corresponding JP Application No. 2010-507486.
Kastin et al. "Neuregulin-1-61 Enters Brain and Spinal Cord by Receptor-Mediated Transport." J. Neurochem. 88.4(2004):965-970.
Kim. "Targeted Molecular Imaging." Korean J. Radio'. 4.4(2003):201-210.
Kubo et al. "Prevalence, Clinical Significance, and Genetic Basis of Hypertrophic Cardiomyopathy With Restrictive Phenotype." J. Am. Coll. Cardiol. 49(2007):2419-2426.
Kumarapeli et al. "A Novel Transgenic Mouse Model Reveals Deregulation of the Ubiquitin-Proteasome System in the Heart by Doxorubicin." FASEB J. 19.14(2005):2051-2053.
Langer et al. "Chemical and Physical Structure of Polymers as Carriers for Controlled Release of Bioactive Agents: A Review." Rev. Macromol. Chem. Phys. 23.1(1983):61-126.
Langer. "New Methods of Drug Delivery." Science. 249(1990):1527-1533.
Latif et al. "Changes in Sarcomeric and Non-Sarcomeric Cytoskeletal Proteins and Focal Adhesion Molecules During Clinical Myocardial Recovery After Left Ventricular Assistn Device Support." J. Heart Lung Transplant. 26(2007):230-235.
Lee et al. "Requirement for Neuregulin Receptor erbB2 in Neural and Cardiac Development." Nature. 378.6555(1995):394-398.
Levy et al. "Inhibition of Calcification of Bioprosthetic Heart Valves by Local Controlled-Release Diphosphonate," Science. 339(1985):190-192.
Li et al. "Interaction of Cardiac Troponin With Cardiotonic Drugs: A Structural Perspective." Biochem. Biophys. Res. Commun. 369(2008):88-99.
Liu et al. "Heterozygous Knockout of Neuregulin-1 Gene in Mice Exacerbates Doxorubicin-Induced Heart Failure." Am. J. Physiol. Heart Cir. Physiol. 289(2005):H660-H666.
Liu et al. "Neuregulin-I/erbB-Activation Improves Cardiac Function and Survival in Models of Ischemic, Dilated, and Viral Cardiomyopathy." J. Am. Coll. Cardiol. 48.7(2006):1438-1447.
Lopez-Berestein. "Treatment of Systemic Fungal Infections With Liposomal-Amphotericin B." *Liposomes in the Therapy of Infectious Disease and Cancer*. Lopez-Berestein et al., eds. New York: Liss. (1989):317-327.
Mexican Office Action issued Jan. 21, 2014, in corresponding MX Application No. MX/a/2009/012174.
Mexican Office Action issued Jan. 25, 2016, in corresponding MX Application No. MX/a/2014/013196.
Mexican Office Action issued Jul. 16, 2015, in corresponding MX Application No. MX/a/2014/013196.
Meyer et al. "Multiple Essential Functions of Neuregulin in Development." Nature. 378(1995):386-390.
Milting et al. "Selective Upregulation of 131-Adrenergic Receptors and Dephosphorylation of Troponin I in End-Stage Heart Failure Patients Supported by Ventricular Assist Devices." Mol. Cell. Cardiol. 41(2006):441-450.

(56) References Cited

OTHER PUBLICATIONS

Nagata et al. "Solution Structure of the Epidermal Growth Factor-Like Domain of Heregulin-a, a Ligand for p180erbB-4." *EMBO J.* 13.15(1994):3517-3523.

Ozcelik et al. "Conditional Mutation of the ErbB2 (HER2) Receptor in Cardiomyocytes Leads to Dilated Cardiomyopathy." *PNAS.* 99.13(2002):8880-8885.

Panjrath et al. "Monitoring Chemotherapy-Induced Cardiotoxicity: Role of Cardiac Nuclear Imaging." *J. Nucl. Cardiol.* 13.3(2006):415-426.

Poizat et al. "Phosphorylation-Dependent Degradation fp300 by Doxorubicin-Activated p38 Mitogen-Activated Protein Kinase in Cardiac Cells." *Mol. Cell. Biol.* 25.7(2005):2673-2687.

Pye et al. (Am. J. Physiol. Heart Circ Physiol. 2003 vol. 284, p. H919-H926).

Ricchiuti et al. "Cardiac Troponin I and T Alterations in Hearts With Severe Left Ventricular Remodeling." *Clin. Chem.* 43.6(1997):990-995.

Rifai et al. "Cardiac Troponin T and I, Echocardiographic Wall Motion Analyses, End Ejection Fractions in Athletes Participating in the Hawaii Ironman Triathlon." *Am. J. Cardiol.* 83.7(1999):1085-1089.

Robinson et al. "Dilated and Hypertrophic Cardiomyopathy Mutations in Troponin and α-Tropomyosin Have Opposing Effects on the Calcium Affinity of Cardiac Thin Filaments." *Circ. Res.* 101(2007):1266-1273.

Saudek et al. "A Preliminary Trial of the Programmable Implantable Medication System for Insulin Delivery." *N. Eng. J. Med.* 321.9(1989):574-579.

Sawyer et al. "Neuregulin-113 for the Treatment of Systolic Heart Failure." J. Mol. Cell Cardiol. 51.4(2011):501-505.

Sefton. "Implantable Pumps." *Crit. Rev. Biomed. Eng.* 14.3(1987):201-240.

Solaro. "Translational Medicine With a Capital T, Troponin T, That is." Circ. Res. 101(2007)114-115.

Solzin et al. "Kinetic Mechanism of the Ca2+-Dependent Switch-On and Switch-Off of Cardiac Troponin in Myofibrils." *Biophys. J.* 93(2007):3917-3931.

Stewart et al. "More 'Malignant' Than Cancer? Five-Year Survival Following a First Admission for Heart Failure." *Eur. J. Heart Fail.* 3.3(2001):315-322.

Sutherland et al. "Neuroprotection for Ischaemic Stroke: Translation From the Bench to the Bedside." Int. J. Stroke. 7.5(2012):407-418.

Treat et al. "Liposome Encapsulated Doxorubicin Preliminary Results of Phase I and Phase II Trials." *Liposomes in the Therapy of Infectious Disease and Cancer.* Lopez-Berestein et al., eds. New York: Liss. (1989):353-365.

VanBuren et al. "Thin Filament Remodeling in Failing Myocardium." *Heart Fail. Rev.* 10(2005):199-209.

Vatutin et al. "Diagnosis of Antracycline-Induced Heart Damages." *Ukrainskii Revmatologicheskii Zhurnal.* 1.3(2001):11-16. (English Abstract Only).

Vatutin et al. "Diagnosis of Antracycline-Induced Heart Damages." *Ukrainskii Revmatologicheskii Zhurnal.* 1.3(2001):11-16. (English Summary).

Veinot. "Diagnostic Endomyocardial Biopsy—Still Useful After All These Years." *Can. J. Cardiol.* 25.2(2009):e55-e56.

Weissleder et al. "Molecular Imaging." *Radiol.* 219(2001):319-333.

Wen et al. "Functional Consequences of the Human Cardiac Troponin I Hypertrophic Cardiomyopathy Mutation R145G in Transgenic Mice." *J. Biol. Chem.* 283(2008):20484-20494.

Wen et al. "Neu Differentiation Factor: A Transmembrane Glycoprotein Containing an EGF Domain and an Immunoglobulin Homology Unit." *Cell.* 69.3(1992):559-572.

Wu et al. "Receptor-Mediated in vitro Gene Transformation by a Soluble DNA Carrier System." *J. Biol. Chem.* 262.10(1987):4429-4432.

Xu et al. "Extended Therapeutic Window and Functional Recovery After Intraarterial Administration of Neuregulin-1 After Focal Ischemic Stroke." J. Cerebral Blood Flow Metab. 26(2006):527-535.

Figure 6A

Nucleotide Sequence & Deduced Acid Sequence of GGF2HBS5

```
GGAATTCCTT TTTTTTTTT TTTTTTTTT NTTTTTTTT TGCCCTTATA CCTCTTCGCC       60
TTTCTGTGGT TCCATCCACT TCTTCCCCCT CCTCCTCCCA TAAACAACTC TCCTACCCCT   120
GCACCCCAA  TAAATAAATA AAAGGAGGAG GGCAAGGGGG GAGGAGGAGG AGTGGTGCTG   180
CGAGGGAAAG GAAAAGGGAG GCAGCGGGAG AAGAGCCGGG CAGAGTCCGA ACCGACAGCC   240
AGAAGCCCGC AGGCACCTCG CACC ATG AGA AGA TGG CGA CGC GCC CCG CGC CGC   291
                            Met Arg Arg Trp Arg Arg Ala Pro Arg Arg

TCC GGG CGT CCC GGC GCC CGG CAG CGC CCC GGC TCC CTG CGC GCC CGC    339
Ser Gly Arg Pro Gly Ala Arg Gln Arg Pro Gly Ser Leu Arg Ala Arg

TCG CCG CCG CTG CCG CTA CTG CCA CTA CTG CTG CTG CTG CTG GGG ACC    387
Ser Pro Pro Leu Pro Leu Leu Pro Leu Leu Leu Leu Leu Leu Gly Thr
                                          Val Cys Leu Leu Thr Val
                                                    GGF-II 09

GCG GCC CTG GGG CCG GGG GCG GCC GCC GGC AAC GAG GCT CCC GCG        435
Ala Ala Leu Gly Pro Gly Ala Ala Ala Gly Asn Glu Ala Ala Pro Ala
Ala Ala Leu Pro Pro

GGG GCC TCG GTG TGC TAC TCG TCC CCC AGC GTG GGA TCG GTG CAG        483
Gly Ala Ser Val Cys Tyr Ser Ser Pro Ser Val Gly Ser Val Gln
                                  Ala Ser Pro Val Gly Ser Val Gln
                                                    GGF-II 08

GAG CTA GCT CAG CGC.GCC GCG GTG ATC GAG GGA AAG GTG CAC CCG        531
Glu Leu Ala Gln Arg Ala Ala Val Ile Glu Gly Lys Val His Pro
Glu Leu Val Gln Arg Trp Phe Val Ile Gln Gly Lys
                         GGF-II 04
```

Figure 6B

Nucleotide Sequence & Deduced Acid Sequence of GGF2HBS5

```
CAG CGG CAG CAG GGG GCA CTC GAC AGG AAG GCG GCG GCG GCG    579
Gln Arg Gln Gln Gly Ala Leu Asp Arg Lys Ala Ala Ala Ala

GGC GAG GGA GGG GCG TGG GGC GAT CGC GAG CCG CCA GCC GCG GGC    627
Gly Glu Ala Gly Ala Trp Gly Asp Arg Glu Pro Pro Ala Ala Gly

CCA CGG GCC CTG GGG CCC CCC GAG GAG CCG GCC CTC GCC GCC AAC    675
Pro Arg Ala Leu Gly Pro Pro Glu Glu Pro Ala Leu Ala Ala Asn

GGG ACC GTG CCC TCT TGG CCC ACC GCC CCG GTG CCC AGC GGC GAG    723
Gly Thr Val Pro Ser Trp Pro Thr Ala Pro Val Pro Ser Ala Gly Glu

CCC GGG GAG GCG CCC TAT CTG AAG GTC GTG CAG TGG TGG GCG    771
Pro Gly Glu Ala Pro Tyr Leu Val Lys Val His Gln Val Trp Ala
                                    Lys Val His Glu Val Trp Ala
                                    GGF-II 01 & GGF-II 11

GTG AAA GCC GGG GGC TTG AAG AAG GAC TCG CTG CTC ACC GTG CGC CTG    819
Val Lys Ala Gly Gly Leu Lys Lys Asp Ser Leu Leu Thr Val Arg Leu
                                    Asp Leu Leu Leu Xaa Val Leu
                                    GGF-II 10

GGG ACC TGG GGC CAC CCC GCC TTC CCC TCC TGC GGG AGG CTC AAG GAG    867
Gly Thr Trp Gly His Pro Ala Phe Pro Ser Cys Gly Arg Leu Lys Glu
Gly Ala Trp Gly Pro Pro Ala Phe Pro Ala Val Xaa Tyr
GGF-II 03

GAC AGC AGG TAC ATC TTC TTC ATG GAG CCC GAC AAC AGC ACC AGC    915
Asp Ser Arg Tyr Ile Phe Phe Met Glu Pro Asp Asn Ser Thr Ser
        Tyr Ile Phe Phe Met Glu Pro Gly Ala Xaa Ser Ser Gly
        GGF-II 02
```

Figure 6C

Nucleotide Sequence & Deduced Acid Sequence of GGF2HBS5

```
CGC GCG CCG GCC GCC TTC CGA GCC TCT TTC CCC CCT CTG GAG ACG GGC      963
Arg Ala Pro Ala Ala Phe Arg Ala Ser Phe Pro Pro Leu Glu Thr Gly

CGG AAC CTC AAG AAG GAG GTC AGC GTG CTG TGC AAG CGG TGC GCC         1011
Arg Asn Leu Lys Lys Glu Val Ser Val Leu Cys Lys Arg Cys Ala

TTG CCT CCC CAA TTG CTA AAA GAG ATG AAA AGC CAG GAA TCG GCT GCA GGT  1059
Leu Pro Pro Gln Leu Leu Lys Glu Met Lys Ser Gln Glu Ser Ala Ala Gly

TCC AAA CTA GTC CTT CGG TGT GAA ACC AGT TCT GAA TAC TCC TCT CTC     1107
Ser Lys Leu Val Leu Arg Cys Glu Thr Ser Ser Glu Tyr Ser Ser Leu
Leu Val Leu Arg
GGF-II 06

AGA TTC TGG TTC AAG AAT GGG AAT GAA TTG AAT CGA AAA AAC AAA         1155
Arg Phe Trp Phe Lys Asn Gly Asn Glu Leu Asn Arg Lys Asn Lys

CCA CAA AAT ATC AAG ATA CAA ATA CAG TTG AAG CCA GGG AAG TCA GAA CTT CGC  1203
Pro Gln Asn Ile Lys Ile Gln Ile Gln Leu Lys Pro Gly Lys Ser Glu Leu Arg

ATT AAC AAA GCA TCA CTG GCT GAT TCT GGA GAG TAT ATG TGC AAA GTG     1251
Ile Asn Lys Ala Ser Leu Ala Asp Ser Gly Glu Tyr Met Cys Lys Val
      Lys Ala Ser Leu Ala Asp Ser Gly Glu Tyr Met Xaa Lyx
                              GGF-II 12

ATC AGC AAA TTA GGA AAT GAC AGT GCC TCT GCC AAT ATC ACC ATC GTG     1299
Ile Ser Lys Leu Gly Asn Asp Ser Ala Ser Ala Asn Ile Thr Ile Val

GAA TCA AAC GCT ACA TCT ACA TCC ACC ACT GGG ACA AGC CAT CTT GTA     1347
Glu Ser Asn Ala Thr Ser Thr Ser Thr Thr Gly Thr Ser His Leu Val
```

Figure 6D

Nucleotide Sequence & Deduced Acid Sequence of GGF2HBS5

```
AAA TGT GCG GAG AAG GAG AAA ACT TTC TGT GTG AAT GGA GGG GAG TGC     1395
Lys Cys Ala Glu Lys Glu Lys Thr Phe Cys Val Asn Gly Gly Glu Cys

TTC ATG GTG AAA GAC CTT TCA AAC CCC TCG AGA TAC TTC TGC AAG TGC     1443
Phe Met Val Lys Asp Leu Ser Asn Pro Ser Arg Tyr Phe Cys Lys Cys

CCA AAT GAG TTT ACT GGT GAT CGC TGC CAA AAC TAC GTA ATG GCC AGC     1491
Pro Asn Glu Phe Thr Gly Asp Arg Cys Gln Asn Tyr Val Met Ala Ser

TTC TAC AGT ACG TCC ACT CCC TTT CTG TCT CTG CCT GAA                 1530
Phe Tyr Ser Thr Ser Thr Pro Phe Leu Ser Leu Pro Glu

TAGGAGCATG CTCAGTTGGT GCTGCTTTCT TGTTGCTGCA TCTCCCCTCA GATTCCACCT   1590

AGAGCTAGAT GTGTCTTACC AGAATCTAATA TTGACTGCCT CTGCCTGTCG CATGAGAACA  1650

TTAACAAAAG CAATTGTATT ACTTCCTCTG TTCCGACTA GTTGGCTCTG AGATACTAAT   1710

AGTGTGTCTGA GGCTCCGGAT GTTTCTCGAA TTGATATTGA ATGATGTGAT ACAAATTGAT 1770

AGTCAATATC AAGCAGTGAA ATATGATAAT AAAGGCATTT CAAAGTCTCA CTTTTATTGA  1830

TAAAATAAAA ATCATTCCTAC TGAACAGTCC ATCTTCTTTA TACAATGACC ACATCCTGAA 1890

AAGGGTGTTG CTAAGCTGTA ACCGATATGC ACTTGAAAATG ATGGTAAGTT AATTTGATT  1950

CAGAATGTGT TATTTGTCAC AAATAACAT AATAAAAGGA AAAAAAAAA AAA            2003
```

Figure 7

EGFL1

| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |

| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |

| TTG | TGC | AAG | TGC | CCA | AAT | GAG | TTT | ACT | GGT | GAT | CGC | TGC | CAA | AAC | TAC | 144 |
| Leu | Cys | Lys | Cys | Pro | Asn | Glu | Phe | Thr | Gly | Asp | Arg | Cys | Gln | Asn | Tyr | |

| GTA | ATG | GCC | AGC | TTC | TAC | AGT | ACG | TCC | ACT | CCC | TTT | CTG | TCT | CTG | CCT | 192 |
| Val | Met | Ala | Ser | Phe | Tyr | Ser | Thr | Ser | Thr | Pro | Phe | Leu | Ser | Leu | Pro | |

| GAA | TAG | | | | | | | | | | | | | | | 198 |
| Glu | | | | | | | | | | | | | | | | |

Figure 8

EGFL2

| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |

| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |

| TTG | TGC | AAG | TGC | CAA | CCT | GGA | TTC | ACT | GGA | GCG | AGA | TGT | ACT | GAG | AAT | 144 |
| Leu | Cys | Lys | Cys | Gln | Pro | Gly | Phe | Thr | Gly | Ala | Arg | Cys | Thr | Glu | Asn | |

| GTG | CCC | ATG | AAA | GTC | CAA | ACC | CAA | GAA | AAA | GCG | GAG | CTC | TAC | TAA | | 192 |
| Val | Pro | Met | Lys | Val | Gln | Thr | Gln | Glu | Lys | Ala | Glu | Leu | Tyr | | | |

Figure 9

EGFL3

| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |

| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |

| TTG | TGC | AAG | TGC | CCA | AAT | GAG | TTT | ACT | GGT | GAT | CGC | TGC | CAA | AAC | TAC | 144 |
| Leu | Cys | Lys | Cys | Pro | Asn | Glu | Phe | Thr | Gly | Asp | Arg | Cys | Gln | Asn | Tyr | |

| GTA | ATG | GCC | AGC | TTC | TAC | AAA | GCG | GAG | CTC | TAC | TAA | | | | | 183 |
| Val | Met | Ala | Ser | Phe | Tyr | Lys | Ala | Glu | Leu | Tyr | | | | | | |

Figure 10

EGFL4

| | | | | | | | | | | | | | | | |
|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn |

| GGA | GGC | GAG | TGC | TTC | ATG | GTC | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr |

| TTG | TGC | AAG | TGC | CCA | AAT | GAG | TTT | ACT | GGT | GAT | CGC | TGC | CAA | AAC | TAC | 144 |
| Leu | Cys | Lys | Cys | Pro | Asn | Glu | Phe | Thr | Gly | Asp | Arg | Cys | Gln | Asn | Tyr |

| GTA | ATG | GCC | AGC | TTC | TAC | AAG | CAT | CTT | GGG | ATT | GAA | TTT | ATG | GAG | AAA | 192 |
| Val | Met | Ala | Ser | Phe | Tyr | Lys | His | Leu | Gly | Ile | Glu | Phe | Met | Glu | Lys |

| GCG | GAG | GAG | CTC | TAC | TAA | | | | | | | | | | | 210 |
| Ala | Glu | Glu | Leu | Tyr | | | | | | | | | | | |

Figure 11

EGFL5

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT   192
Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC   240
Gly Asp Arg Cys Gln Asn Tyr Val Met Ala Ser Phe Tyr Ser Thr Ser

ACT CCC TTT CTG TCT CTG CCT GAA TAG                                267
Thr Pro Phe Leu Ser Leu Pro Glu
```

Figure 12

EGFL6

| | | | | | | | | | | | | | | | |
|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT |
| Ser | His | Leu | Val | Lys | Cys | Ala | Glu | Lys | Glu | Lys | Thr | Phe | Cys | Val | Asn | 48 |
| GGA | GGC | GAG | TGC | TTC | ATG | GTG | AAA | GAC | CTT | TCA | AAT | CCC | TCA | AGA | TAC |
| Gly | Gly | Glu | Cys | Phe | Met | Val | Lys | Asp | Leu | Ser | Asn | Pro | Ser | Arg | Tyr | 96 |
| TTC | TGC | AAG | TGC | CAA | CCT | GGA | TTC | ACT | GGA | GCG | AGA | TGT | ACT | GAG | AAT |
| Leu | Cys | Lys | Cys | Gln | Pro | Gly | Phe | Thr | Gly | Ala | Arg | Cys | Thr | Glu | Asn | 144 |
| GTG | CCC | ATG | AAA | GTC | CAA | ACC | CAA | GAA | AAG | TGC | CCA | AAT | GAG | TTT | ACT |
| Val | Pro | Met | Lys | Val | Gln | Thr | Gln | Glu | Lys | Cys | Pro | Asn | Glu | Phe | Thr | 192 |
| GGT | GAT | CGC | TGC | CAA | AAC | TAC | GTA | ATG | GCC | TTC | TAC | AAA | GCG | GAG |
| Gly | Asp | Arg | Cys | Gln | Asn | Tyr | Val | Met | Ala | Ser | Phe | Tyr | Lys | Ala | Glu | 240 |
| GAG | CTC | TAC | TAA |
| Glu | Leu | Tyr | | | | | | | | | | | | | | 252 |

SEQUENCE LISTING

<160> NUMBER OF SEQ ID NOS: 14

<210> SEQ ID NO 1
<211> LENGTH: 2003
<212> TYPE: DNA
<213> ORGANISM: Homo sapiens

<400> SEQUENCE: 1
ggaattcctt tttttttttt tttttttctt rrtttttttt tgcccttata cctcttcgcc    60

-continued

| | |
|---|---|
| tttctgtggt tccatccact tcttcccct cctcctccca taaacaactc tcctacccct | 120 |
| gcacccccaa taaataaata aaaggaggag ggcaaggggg gaggaggagg agtggtgctg | 180 |
| cgagggaag gaaaagggag gcagcgcgag aagagccggg cagagtccga accgacagcc | 240 |
| agaagcccgc acgcacctcg caccatgaga tggcgacgcg cccgcgccg ctccgggcgt | 300 |
| cccggccccc gggcccagcg ccccggctcc gccgcccgct cgtcgccgcc gctgccgctg | 360 |
| ctgccactac tgctgctgct ggggaccgcg gccctggcgc cggggcggc ggccggcaac | 420 |
| gaggcggctc ccgcggggc ctcggtgtgc tactcgtccc cgcccagcgt gggatcggtg | 480 |
| caggagctag ctcagcgcgc cgcggtggtc atcgagggaa aggtgcaccc gcagcggcgg | 540 |
| cagcagggg cactcgacag gaaggcggcg gcggcggcg gcgaggcagg ggcgtggggc | 600 |
| ggcgatcgcg agccgccagc cgcgggccca cgggcgctgg ggccgcccgc cgaggagccg | 660 |
| ctgctcgccg ccaacgggac cgtgccctct tggcccaccg ccccggtgcc cagcgccggc | 720 |
| gagccccggg aggaggcgcc ctatctggtg aaggtgcacc aggtgtgggc ggtgaaagcc | 780 |
| gggggcttga agaaggactc gctgctcacc gtgcgcctgg ggacctgggg ccaccccgcc | 840 |
| ttcccctcct gcgggaggct caaggaggac agcaggtaca tcttcttcat ggagcccgac | 900 |
| gccaacagca ccagccgcgc gccggccgcc ttccgagcct cttcccccc tctggagacg | 960 |
| ggccggaacc tcaagaagga ggtcagccgg gtgctgtgca agcggtgcgc cttgcctccc | 1020 |
| caattgaaag agatgaaaag ccaggaatcg gctgcaggtt ccaaactagt ccttcggtgt | 1080 |
| gaaaccagtt ctgaatactc ctctctcaga ttcaagtggt tcaagaatgg gaatgaattg | 1140 |
| aatcgaaaaa acaaaccaca aaatatcaag atacaaaaaa agccagggaa gtcagaactt | 1200 |
| cgcattaaca aagcatcact ggctgattct ggagagtata tgtgcaaagt gatcagcaaa | 1260 |
| ttaggaaatg acagtgcctc tgccaatatc accatcgtgg aatcaaacgc tacatctaca | 1320 |
| tccaccactg ggacaagcca tcttgtaaaa tgtgcggaga aggagaaaac tttctgtgtg | 1380 |
| aatggaggg agtgcttcat ggtgaaagac ctttcaaacc cctcgagata cttgtgcaag | 1440 |
| tgcccaaatg agtttactgg tgatcgctgc caaaactacg taatggccag cttctacagt | 1500 |
| acgtccactc cctttctgtc tctgcctgaa taggagcatg ctcagttggt gctgctttct | 1560 |
| tgttgctgca tctcccctca gattccacct agagctagat gtgtcttacc agatctaata | 1620 |
| ttgactgcct ctgcctgtcg catgagaaca ttaacaaaag caattgtatt acttcctctg | 1680 |
| ttcgcgacta gttggctctg agatactaat aggtgtgtga ggctccggat gtttctggaa | 1740 |
| ttgatattga atgatgtgat acaaattgat agtcaatatc aagcagtgaa atatgataat | 1800 |
| aaaggcattt caaagtctca cttttattga taaaataaaa atcattctac tgaacagtcc | 1860 |
| atcttctta tacaatgacc acatcctgaa aagggtgttg ctaagctgta accgatatgc | 1920 |
| acttgaaatg atggtaagtt aatttttgatt cagaatgtgt tatttgtcac aaataaacat | 1980 |
| aataaaagga aaaaaaaaa aaa | 2003 |

<210> SEQ ID NO 2
<211> LENGTH: 422
<212> TYPE: PRT
<213> ORGANISM: Homo sapiens

<400> SEQUENCE: 2

Met Arg Trp Arg Arg Ala Pro Arg Arg Ser Gly Arg Pro Gly Pro Arg
1               5                   10                  15

Ala Gln Arg Pro Gly Ser Ala Ala Arg Ser Ser Pro Pro Leu Pro Leu
            20                  25                  30

```
Leu Pro Leu Leu Leu Leu Gly Thr Ala Leu Ala Pro Gly Ala
        35                  40                  45

Ala Ala Gly Asn Gly Ala Ala Pro Ala Gly Ala Ser Val Cys Tyr Ser
50                  55                  60

Ser Pro Pro Ser Val Gly Ser Val Gln Glu Leu Ala Gln Arg Ala Ala
65                  70                  75                  80

Val Val Ile Glu Gly Lys Val His Pro Gln Arg Gln Gln Gly Ala
                85                  90                  95

Leu Asp Arg Lys Ala Ala Ala Ala Gly Glu Ala Gly Ala Trp Gly
            100                 105                 110

Gly Asp Arg Glu Pro Pro Ala Ala Gly Pro Arg Ala Leu Gly Pro Pro
            115                 120                 125

Ala Glu Glu Pro Leu Leu Ala Ala Asn Gly Thr Val Pro Ser Trp Pro
130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
            180                 185                 190

Phe Pro Ser Cys Gly Arg Leu Lys Glu Asp Ser Arg Tyr Ile Phe Phe
            195                 200                 205

Met Glu Pro Asp Ala Asn Ser Thr Ser Arg Ala Pro Ala Ala Phe Arg
            210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
                245                 250                 255

Met Lys Ser Gln Glu Ser Ala Ala Gly Ser Lys Leu Val Leu Arg Cys
            260                 265                 270

Glu Thr Ser Ser Glu Tyr Ser Ser Leu Arg Phe Lys Trp Phe Lys Asn
            275                 280                 285

Gly Asn Glu Leu Asn Arg Lys Asn Lys Pro Gln Asn Ile Lys Ile Gln
            290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
                325                 330                 335

Ser Ala Ser Ala Asn Ile Thr Ile Val Glu Ser Asn Ala Thr Ser Thr
            340                 345                 350

Ser Thr Thr Gly Thr Ser His Leu Val Lys Cys Ala Glu Lys Glu Lys
            355                 360                 365

Thr Phe Cys Val Asn Gly Gly Glu Cys Phe Met Val Lys Asp Leu Ser
370                 375                 380

Asn Pro Ser Arg Tyr Leu Cys Lys Cys Pro Asn Glu Phe Thr Gly Asp
385                 390                 395                 400

Arg Cys Gln Asn Tyr Val Met Ala Ser Phe Tyr Ser Thr Ser Thr Pro
                405                 410                 415

Phe Leu Ser Leu Pro Glu
            420

<210> SEQ ID NO 3
<211> LENGTH: 198
```

<212> TYPE: DNA
<213> ORGANISM: Homo sapiens

<400> SEQUENCE: 3

```
agccatcttg tcaagtgtgc agagaaggag aaaactttct gtgtgaatgg aggcgagtgc    60
ttcatggtga aagacctttc aaatccctca agatacttgt gcaagtgccc aaatgagttt   120
actggtgatc gctgccaaaa ctacgtaatg ccagcttct acagtacgtc cactccctt    180
ctgtctctgc ctgaatag                                                 198
```

<210> SEQ ID NO 4
<211> LENGTH: 65
<212> TYPE: PRT
<213> ORGANISM: Homo sapiens

<400> SEQUENCE: 4

```
Ser His Leu Val Lys Cys Ala Glu Lys Glu Lys Thr Phe Cys Val Asn
1               5                   10                  15
Gly Gly Glu Cys Phe Met Val Lys Asp Leu Ser Asn Pro Ser Arg Tyr
            20                  25                  30
Leu Cys Lys Cys Pro Asn Glu Phe Thr Gly Asp Arg Cys Gln Asn Tyr
        35                  40                  45
Val Met Ala Ser Phe Tyr Ser Thr Ser Thr Pro Phe Leu Ser Leu Pro
    50                  55                  60
Glu
65
```

<210> SEQ ID NO 5
<211> LENGTH: 192
<212> TYPE: DNA
<213> ORGANISM: Homo sapiens

<400> SEQUENCE: 5

```
agccatcttg tcaagtgtgc agagaaggag aaaactttct gtgtgaatgg aggcgagtgc    60
ttcatggtga aagacctttc aaatccctca agatacttgt gcaagtgcca acctggattc   120
actggagcga gatgtactga gaatgtgccc atgaaagtcc aaacccaaga aaaagcggag   180
gagctctact aa                                                       192
```

<210> SEQ ID NO 6
<211> LENGTH: 63
<212> TYPE: PRT
<213> ORGANISM: Homo sapiens

<400> SEQUENCE: 6

```
Ser His Leu Val Lys Cys Ala Glu Lys Glu Lys Thr Phe Cys Val Asn
1               5                   10                  15
Gly Gly Glu Cys Phe Met Val Lys Asp Leu Ser Asn Pro Ser Arg Tyr
            20                  25                  30
Leu Cys Lys Cys Gln Pro Gly Phe Thr Gly Ala Arg Cys Thr Glu Asn
        35                  40                  45
Val Pro Met Lys Val Gln Thr Gln Glu Lys Ala Glu Glu Leu Tyr
    50                  55                  60
```

<210> SEQ ID NO 7
<211> LENGTH: 183
<212> TYPE: DNA
<213> ORGANISM: Homo sapiens

<400> SEQUENCE: 7

```
agccatcttg tcaagtgtgc agagaaggag aaaactttct gtgtgaatgg aggcgagtgc      60
ttcatggtga aagacctttc aaatccctca agatacttgt gcaagtgccc aaatgagttt     120
actggtgatc gctgccaaaa ctacgtaatg gccagcttct acaaagcgga ggagctctac     180
taa                                                                   183
```

```
<210> SEQ ID NO 8
<211> LENGTH: 60
<212> TYPE: PRT
<213> ORGANISM: Homo sapiens

<400> SEQUENCE: 8

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr
    50                  55                  60
```

```
<210> SEQ ID NO 9
<211> LENGTH: 210
<212> TYPE: DNA
<213> ORGANISM: Homo sapiens

<400> SEQUENCE: 9
agccatcttg tcaagtgtgc agagaaggag aaaactttct gtgtgaatgg aggcgagtgc      60
ttcatggtga aagacctttc aaatccctca agatacttgt gcaagtgccc aaatgagttt     120
actggtgatc gctgccaaaa ctacgtaatg gccagcttct acaagcatct tgggattgaa     180
tttatggaga aagcggagga gctctactaa                                      210
```

```
<210> SEQ ID NO 10
<211> LENGTH: 69
<212> TYPE: PRT
<213> ORGANISM: Homo sapiens

<400> SEQUENCE: 10

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe Met Glu Lys
    50                  55                  60

Ala Glu Glu Leu Tyr
65
```

```
<210> SEQ ID NO 11
<211> LENGTH: 267
<212> TYPE: DNA
<213> ORGANISM: Homo sapiens

<400> SEQUENCE: 11
agccatcttg tcaagtgtgc agagaaggag aaaactttct ttcatggtga aagacctttc      60
aaatccctca agatacttgt actggagcga gatgtactga gaatgtgccc atgaaagtcc     120
```

```
aatgagttta ctggtgatcg ctgccaaaac tacgtaatgg actcccttc tgtctctgcc    180 tgaataggtg tgaatggagg cgagtgcgca agtgccaacc tggattcaaa cccaagaaaa    240
gtgcccacca gcttctacag tacgtcc                                        267
```

<210> SEQ ID NO 12
<211> LENGTH: 88
<212> TYPE: PRT
<213> ORGANISM: Homo sapiens

<400> SEQUENCE: 12

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Cys Pro Asn Glu Phe Thr
    50                  55                  60

Gly Asp Arg Cys Gln Asn Tyr Val Met Ala Ser Phe Tyr Ser Thr Ser
65                  70                  75                  80

Thr Pro Phe Leu Ser Leu Pro Glu
                85
```

<210> SEQ ID NO 13
<211> LENGTH: 252
<212> TYPE: DNA
<213> ORGANISM: Homo sapiens

<400> SEQUENCE: 13

```
agccatcttg tcaagtgtgc agagaaggag aaaactttct gtgtgaatgg aggcgagtgc     60
ttcatggtga agaccttc aaatccctca agatacttgt gcaagtgcca acctggattc     120
actggagcga gatgtactga aatgtgccc atgaaagtcc aaacccaaga aaagtgccca    180
aatgagttta ctggtgatcg ctgccaaaac tacgtaatgg ccagcttcta caaagcggag    240
gagctctact aa                                                         252
```

<210> SEQ ID NO 14
<211> LENGTH: 83
<212> TYPE: PRT
<213> ORGANISM: Homo sapiens

<400> SEQUENCE: 14

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Cys Pro Asn Glu Phe Thr
    50                  55                  60

Gly Asp Arg Cys Gln Asn Tyr Val Met Ala Ser Phe Tyr Lys Ala Glu
65                  70                  75                  80

Glu Leu Tyr
```

METHODS FOR DETECTING CARDIAC DAMAGE

CROSS REFERENCE TO RELATED APPLICATION

The present application is a continuation of U.S. patent application Ser. No. 14/153,695, filed Jan. 13, 2014, which is a continuation of U.S. patent application Ser. No. 12/451, 397, filed Mar. 26, 2010 (now U.S. Pat. No. 8,628,929), which is a National Stage Application claiming the priority of PCT Application No. PCT/US2008/006060 filed May 12, 2008, which in turn, claims priority from U.S. Provisional Application No. 60/928,541, filed May 10, 2007. The entire contents of these applications are each incorporated herein by reference in their entireties.

FIELD OF THE INVENTION

The invention relates to the field of medical diagnostics. More particularly, the invention is directed to a method for detecting heart damage in a patient. The invention also relates to methods for treatment of patients identified as having heart damage. The invention also pertains to methods for evaluating the efficacy of an ongoing therapeutic regimen designed to treat a damaged heart in a patient.

BACKGROUND OF THE INVENTION

Several publications and patent documents are referenced in this application in order to more fully describe the state of the art to which this invention pertains. The disclosure of each of these publications and documents is incorporated by reference herein.

Heart failure is causally related to a number of conditions that damage the heart, including coronary heart disease, with or without a heart attack; hypertension; diseases, infections, or toxins that affect the heart muscle; and diseases of the heart valves. The onset of heart failure can occur rapidly, over days to weeks, but more frequently develops slowly over the course of years, as the heart gradually and progressively weakens.

Therapeutic intervention directed to reduction of cancer cell load in a patient frequently, if not always, is accompanied by a range of deleterious side effects. Indeed, cytostatic agents used as chemotherapeutics for the treatment of various cancers frequently exhibit potentially lethal side effects, including cardiotoxicity. Agents commonly used in cytostatic therapy include the anthracyclines daunorubicin and prodrugs thereof, zorubicin, doxorubicin (adriamycin) and epirubicin, and the synthetic antibiotic mitoxantrone. Anthracyclines, for example, represent a class of chemotherapeutic agents based on daunosamine and tetra-hydro-naphthacene-dione. These compounds are used to treat a variety of cancers, including leukemias and lymphomas, and solid tumors of the breast, uterus, ovary, and lung. In addition to the expected adverse reactions observed in patients undergoing chemotherapy, such as hair loss and nausea, therapeutic intervention involving anthracycline administration is complicated and limited by the marked cardiotoxicity of this class of compounds. Cardiotoxicity associated with anthracycline use is correlated with the total dose administered and is frequently irreversible. The cytostatic effects and cardiotoxicity of these compounds are due, at least in part, to alterations in membrane fluidity and permeability caused by anthracycline binding to components of the cell membrane. Free radical formation in the heart and accumulation of anthracycline metabolites are also thought to contribute to heart damage. Cardiotoxicity often presents in electrocardiogram (EKG) abnormalities and arrhythmias or as cardiomyopathy, which may ultimately lead to congestive heart failure.

SUMMARY OF THE INVENTION

The invention is directed to providing novel diagnostic methods for screening patients to identify those exhibiting signs of heart damage. Patients so identified can then be treated with pharmaceutical preparations for the treatment of heart damage as described herein. In a particular aspect of the invention, diagnostic methods for screening patients to identify those exhibiting signs of damage to the heart due to, for example, cardiotoxicity, hypertension, valvular disorders, myocardial infarction, viral myocarditis, or scleroderma are presented. In a particular aspect, the invention is focused on identifying patients exhibiting cardiotoxicity resulting from chemotherapeutic intervention. Classification of such patients serves to identify a subgroup of patients in need of therapeutic intervention to alleviate short and long term effects of cardiotoxicity. The subgroup of patients so identified can be treated with pharmaceutical preparations for the treatment of heart damage that occurs in connection with the use of cardiotoxic doses of medicaments or chemicals. Under circumstances wherein the heart damage identified in a patient is due to an ongoing condition, such as, hypertension, valvular disorders, myocardial infarction, viral myocarditis, scleroderma, appropriate pharmaceutical preparations can also be formulated to treat the patient with heart damage.

The present invention also encompasses a method for stratifying patients according to degree or type of heart damage, knowledge of which guides a skilled practitioner to choose appropriate therapeutic regimens. The invention also includes a method whereby the efficacy of a therapeutic regimen is evaluated.

The novel methods of the invention are based on the discovery that changes in intracellular levels of cardiac troponin I (cTnI) and cardiac troponin T (cTnT) in intact cardiac tissue can be used as indicators for the presence of cardiac damage. More specifically, the present inventors have discovered that a decrease in intracellular cTnI and cTnT levels in intact cardiac tissue serves as a diagnostic marker to identify patients at risk for or experiencing cardiac damage. Cardiac tissue can be excised from a patient and tested in vitro or analyzed in vivo using molecular imaging protocols known in the art.

Using either approach, intracellular cTnI and cTnT levels determined for the patient's cardiac tissue are compared to those of control cardiac tissue that expresses wildtype or normal levels of intracellular cTnI and cTnT. Reduced levels of intracellular cTnI and/or cTnT in a patient's cardiac tissue are readily determined by quantitating protein levels, which can be achieved using standard methods, and analyzing the results to determine if a statistically significant decrease in intracellular cTnI and cTnT levels is apparent in the patient's cardiac tissue relative to that of the control. Patients showing evidence of reduced intracellular cTnI and/or cTnT levels are earmarked for treatment with appropriate compositions chosen to restore, at least in part, normal heart function as reflected in an increase in intracellular cTnI and cTnT levels or restoration of normal levels of intracellular cTnI and cTnT.

In an embodiment of the present invention, the control or normal intracellular levels of either cTnT or cTnI in cardiac tissue are established by determining the intracellular levels of either cTnT or cTnI in cardiac tissue of a patient with normal heart function. In another embodiment of the present invention, the control or normal intracellular levels of either cTnT or cTnI in cardiac tissue are established by determining the intracellular levels of either cTnT or cTnI in cardiac tissue of a patient prior to onset of treatment capable of causing heart damage.

In an aspect of the present invention, the heart damage is a result of cardiotoxicity, hypertension, valvular disorders, myocardial infarction, viral myocarditis, or scleroderma. In a further aspect of the invention, the cardiotoxicity is caused by treatment with a chemotherapeutic agent or radiation.

It is also within the scope of the invention to evaluate the efficacy of a therapeutic regimen designed to at least partially restore normal heart function by measuring intracellular cTnI and cTnT levels in cardiac tissue of a treated patient. In accordance with the present invention, an increase in intracellular cTnI and cTnT levels in cardiac tissue of a treated patient relative to those determined prior to treatment is a positive indicator that the treatment is acting to restore cardiac function.

It is to be understood that intracellular levels of either cTnI or cTnT in cardiac tissue or intracellular levels of both cTnI and cTnT in cardiac tissue may be used as indicators of cardiac tissue activity and/or function. This applies to all aspects of the invention, including methods directed to evaluating or diagnosing cardiac damage, methods directed to stratifying patients with respect to particular therapeutic regimens, and methods directed to evaluating efficacy of a therapeutic regimen.

In accordance with the present invention decreased levels of cTnI and/or cTnT mRNA in cardiac tissue are also indicative of heart damage and may be used to stratify patient populations. Partial or complete restoration of normal cTnI and/or cTnT mRNA levels is also, therefore, a positive indicator of therapeutic efficacy as described above with respect to protein levels.

The present invention pertains to animals, in general, and more particularly, to mammals, and even more particularly to humans. Accordingly, the subject is preferably an animal, including but not limited to animals such as cows, pigs, horses, chickens, cats, dogs, etc., and is preferably a mammal, and most preferably human. Accordingly, the term "subject" or "patient" may be used to refer to a human.

The present invention also encompasses a combination therapeutic regimen wherein GGF2 or an epidermal growth factor-like (EGFL) domain encoded by the neuregulin gene is administered in conjunction with a proteasome inhibitor to treat cardiac damage. An exemplary proteasome inhibitor for use in the present invention is Proscript 519, which is a potent and selective proteasome inhibitor. Other proteasome inhibitors of utility in the present invention include Velcade™ and lactacystin. Additional proteasome inhibitors are known to those skilled in the art. Indeed, proteasome inhibitors are already used as therapeutic agents for the treatment of a number of diseases, including some cancers and neurodegenerative diseases.

Also encompassed by the present invention is the use of GGF2 or an epidermal growth factor-like (EGFL) domain encoded by the neuregulin gene in the preparation of a medicament for administration to a patient identified by the present diagnostic methods as exhibiting damage to the heart. The invention further encompasses the use of GGF2 or an epidermal growth factor-like (EGFL) domain encoded by the neuregulin gene in combination with a proteasome inhibitor in the preparation of a medicament far administration to a patient identified by the present diagnostic methods as exhibiting damage to the heart.

Other features and advantages of the invention will be apparent from the following description of the preferred embodiments thereof, and from the claims.

BRIEF DESCRIPTION OF THE DRAWINGS

FIG. 1C shows that NRG1 injection alleviated doxorubicin-induced down-regulation of cTnI, cTnT and cTnC protein levels in mice. Mice were treated with doxorubicin (20 mg/kg, i.p.) with or without concomitant NRG1 injection (0.75 mg/kg, s.c. daily). Protein levels of cTnI, cTnT and cTnC were measured by Western blot analysis five days after doxorubicin treatment.

FIG. 2A reveals that NRG1 alleviated doxorubicin-induced down-regulation of cTnI and cTnT protein levels in neonatal rat cardiomyocytes (RNCM). RNCM were treated with doxorubicin (1 uM) in the presence or absence of NRG1 (20 ng/ml or 50 ng/ml). cTnI and cTnT protein levels were measured by Western blot analysis 48 hours after doxorubicin treatment. FIG. 2B shows that, inhibition of erbB2 abolished the effects of NRG1 on cTnI and cTnT. RNCM were treated with doxorubicin (1 uM) and NRG1 (20 ng/ml) in the presence or the absence or A0879 (10 uM) and AG1478 (10 uM). Protein levels of cTnI and cTnT were analyzed by Western blot analysis. As shown in FIG. 2C, RNCM were treated with doxorubicin and NRG1 in the presence of LY294002 (10 uM), Akti (5 uM), PD98059 (50 uM) and Rapamycin (10 nM). cTnI and cTnT protein levels were analyzed by Western blot analysis. FIG. 2D shows that RNCM were treated with doxorubicin or doxorubicin+NRG1 in the presence of cycloheximide (5 ug/ml), Z-VAD (100 uM) or MG132 (10 uM). Protein levels of cTnI and cTnT were measured by Western blot analysis.

FIG. 3A presents results wherein RNCM were treated with doxorubicin (1 uM) in the presence of inhibitors for different caspases (20 uM). The protein levels of cTnI and cTnT were measured by Western blot analysis. FIG. 3B shows the effects of caspase activation in doxorubicin-treated RNCM. Cells were treated with Dox, Dox+NRG1 or Dox+NRG1+LY. Caspase activation was analyzed by the caspase activation assay. FIG. 3C shows that NRG1 decreased doxorubicin-induced cytochrome c release. RNCM were treated with Dox or Dox+NRG1. Cytochrome c release was analyzed by cell fractionation and Western blot analysis. FIG. 3D reveals that NRG1 decreased doxorubicin-induced ubiquitinylation of cTnI. RNCM were treated with Dox or Dox+NRG1. Cell lysates were immunoprecipitated with cTnI antibody and probed with ubiquitin antibody.

FIG. 4A reveals that NRG-1 inhibited doxorubicin-induced down-regulation of mRNA levels of cTnI, cTnT and cardiac specific transcriptional factors. RNCM were treated with Dox or Dox+NRG1. mRNA levels of cTnI, cTnT, GATA4, MEF2c and NKX2.5 were analyzed by quantitative RT-PCR. FIG. 4B shows that NRG1 inhibited doxorubicin-induced dephosphorylation of translational molecules. RNCM were treated with Dox, Dox+NRG1 or Dox+NRG1+LY. The phosphorylation levels of mTOR, P70S6K, S6, 4EBP and EIF4G were analyzed by Western blot analysis.

FIG. 5A shows a survival analysis in doxorubicin-treated mice with cardiac myocyte-specific overexpression of a dominant negative PI3K (dnPI3K). Mice were treated with a single dose of doxorubicin (20 mg/kg, i.p.) with or without concomitant treatment of NRG1 (0.75 mg/kg, s.c.). Fourteen-day survival was analyzed by the Kaplan-Meier method. FIG. 5B depicts hemodynamic measurements in doxorubicin-treated dnPI3K mice. Mice were treated with a single dose of doxorubicin (20 mg/kg, i.p.). Hemodynamic measurements were performed six days after the doxorubicin treatment. FIG. 5C shows cTnI protein levels in dnPI3K mice treated with Dox or Dox+NRG1.

FIGS. 6A-D show amino acid and nucleic acid sequences of GGF2.

FIG. 7 shows amino acid and nucleic acid sequences of EGFL1.

FIG. 8 shows amino acid and nucleic acid sequences of EGFL2.

FIG. 9 shows amino acid and nucleic acid sequences of EGFL3.

FIG. 10 shows amino acid and nucleic acid sequences of EGFL4.

FIG. 11 shows amino acid and nucleic acid sequences of EGFL5.

FIG. 12 shows amino acid and nucleic acid sequences of EGFL6.

DETAILED DESCRIPTION OF THE INVENTION

Figure 1A:
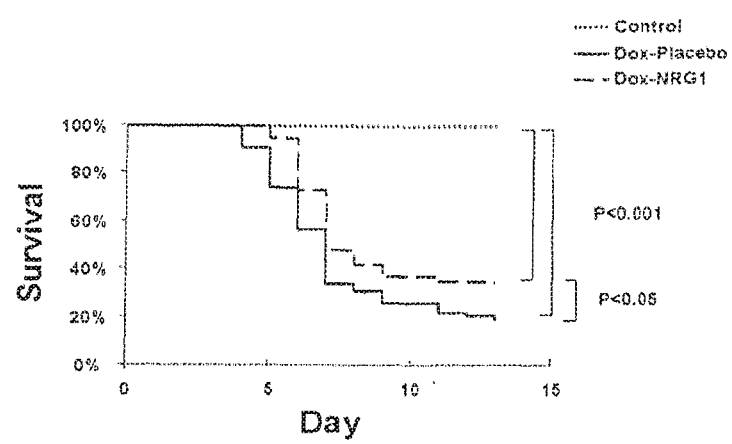
FIGS. 1A-1C show survival graphs (A), histograms (B-C), and immunoblots (C). For the survival analysis (A), mice were injected with a single dose of doxorubicin [20 mg/kg, intraperitoneally (i.p.)] with or without concomitant injection of NRG1 (0.75 mg/kg, s.c. daily). Fourteen day survival was analyzed by the Kaplan-Meier method. With respect to a determination of serum creatine kinase (CK) levels (B), serum CK levels were measured in control, Dox-treated and Dox-NRG1 treated mice four days after doxorubicin injection.

Typically, when a patient arrives at a hospital complaining of chest pain, the following diagnostic steps are taken to evaluate the condition of the patient's heart, and determine the severity of any problems identified. To begin, the patient is interviewed to compile a comprehensive list of symptoms so that a health care professional can rule out non-heart related problems. Second, an electrocardiogram (EKG) reading is taken, which records the electrical waves made by the heart. The EKG is an essential tool for determining the severity of chest pains associated with heart conditions and measuring the degree of damage to the heart. Blood tests are also performed to detect elevated serum levels of certain factors, such as the troponins and creatine kinase (CK), and the more cardiac specific isoform of creatine kinase (CK-MB), which are indicative of heart damage. The rise in serum levels of CK, CK-MB, and the troponins is due to the release of these molecules following cardiac muscle cell death and serves, therefore, as a serum marker of necrosis. As a heart muscle cell dies as a result of prolonged ischemia, for example, the cell membrane ruptures, releasing the cytosolic contents into the extracellular fluid space, from whence it enters the lymphatic system, and subsequently the bloodstream. Imaging tests, including echocardiogram and perfusion scintigraphy, may also be used in the context of diagnosis.

The most specific markers of cardiac necrosis available are the cardiac troponins. These proteins are components of the contractile apparatus of myocardial cells. Two cardiac troponins, cTnI and cTnT, have been commercialized and detection of these markers has proven to be a reliable and specific assay for detection of minimal levels of myocardial damage. The cardiac troponins, like CK-MB, are released from dead cardiac muscle cells upon rupture of cell membranes, and are eventually detectable in the blood. Necrosis can occur as a result of a prolonged myocardial ischemia, but can also result from myocardial cell damage from other causes such as infection, trauma, or congestive heart failure.

The present invention differs from those procedures described in the prior art in a variety of aspects. At the outset, it is directed to measuring intracellular levels of cTnI and cTnT in intact cardiac tissue, rather than serum levels of these markers. Moreover, the present inventors have discovered that a decrease in intracellular cTnI and cTnT levels in intact cardiac tissue serves as a diagnostic marker to identify patients at risk for or experiencing cardiac damage. This approach stands in marked contrast to measurements of serum levels of these markers, an increase of which is indicative of heart damage. Moreover, an increase in serum levels of these markers is an acute or transient marker of heart damage, whereas measurements of intracellular levels of cTnI and cTnT in intact cardiac tissue serves as a stable marker reflective of the condition of the heart. In accordance with the present invention, identification of patients exhibiting a decrease in intracellular cTnI and cTnT levels in intact cardiac tissue also provides a screening method with which to stratify patients into categories for subsequent treatment. Patients showing evidence of reduced intracellular cTnI and cTnT levels are earmarked for treatment with appropriate compositions chosen to restore, at least in part, normal heart function as reflected in restoration of such.

An exemplary therapeutic agent for inclusion in such a composition is glial growth factor 2 (GGF2). The amino acid and nucleic acid sequences of GGF2 are presented in FIGS. 6A-6D. Therapeutic compositions may also include other exemplary polypeptides, such as epidermal growth factor-like (EGFL) domains encoded by the neuregulin gene, as shown in FIGS. 7-12, and described in U.S. Pat. No. 5,530,109, which is incorporated herein in its entirety.

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The compositions containing the molecules or compounds of the invention can be administered for diagnostic and/or therapeutic treatments. In diagnostic applications, compositions are administered to a patient to determine if the patient has cardiac damage and/or to stratify the patient with respect to prospective therapeutic regimens. In therapeutic applications, compositions are administered to a patient diagnosed as having cardiac damage in an amount sufficient to treat the patient, thereby at least partially arresting the symptoms of the disease and its complications. An amount adequate to accomplish this is defined as a "therapeutically effective amount or dose." Amounts effective for this use will depend on the severity of the disease and the weight and general state of the patient.

As used herein, the phrase "control sample of cardiac tissue" refers to a sample of cardiac tissue for which intracellular levels of cTnI and cTnT are within normal range. A normal or wildtype range of intracellular levels of cTnI and cTnT is established based on experiments such as those presented herein and known in the art wherein cardiac tissue of a subject having healthy heart function, as determined by a skilled practitioner, is used as the standard against which unknowns are compared. Standards, representative of normal hearts, may, for example, be procured from fresh autopsies performed on cadavers having no evidence of heart disease.

Similarly, the term "control or normal levels" refers to levels established or determined as described rein and understood in the art to be within a range associated with healthy functionality. With respect to the present invention, healthy functionality refers to healthy heart function, which can be assessed by a skilled practitioner using standard procedures such as measuring systolic and diastolic blood pressure, measuring serum levels of indicator proteins such as CK, CK-MB, and the troponins, performing an EKG, and/or administering a stress test. A skilled practitioner would be aware of that which is generally considered a normal serum level of these proteins.

Various studies have been presented with respect to serum CK levels, for example, and general guidelines have been established. In one such study, for example, patients with suspected myocardial infarction (MI) who had a serum creatine kinase level of 280 IU/L or more were very likely to have had an MI; patients with a serum creatine kinase level of 80 to 279 IU/L were likely to have had an MI; patients with a creatine kinase level of 40 to 79 IU/L were less likely to have had an MI; and patients with a creatine kinase level of less than 40 IU/L were much less likely to have had an MI. With respect to that which is considered a normal serum level of CK or troponins, it is to be understood that different hospitals have established standards that vary slightly. Moreover, a skilled practitioner would be cognizant of the accepted standard in the particular clinical setting (e.g., particular hospital) in which the practitioner is working.

Troponin is also recognized as a sensitive and specific marker for cardiac injury. Indeed, detection of serum troponin 1 (sTnI) is considered to be more accurate than creatine kinase-MB concentrations for the diagnosis of MI and provides more useful prognostic information. Detection of sTnI also permits the early identification of those patients with acute coronary syndromes who are at an increased risk of death. sTnI is more sensitive than creatine kinase-MB concentrations for detection of minor ischemic myocardial injury in patients with small increases of total creatine kinase and avoids the high incidence of false diagnoses associated with the use of creatine kinase-MB as a diagnostic marker in perioperative MI. In one study, for example, patients with moderate elevations of serum troponin I (0.4-2.0 µg/L) had a significantly higher mortality rate and longer length of intensive care unit and hospital stays when compared with patients without similar elevations. Within the range of moderately elevated troponin concentrations, higher titers were associated with increasing mortality risk, longer hospital and intensive care unit stays, and a higher incidence of myocardial infarction. Treatment of patients exhibiting maximum serum troponin concentrations equal to or greater than 2 µg/L with β-blockers and aspirin improved their prognosis.

With respect to normal levels of intracellular cTnI and cTnT, such determinations are established by evaluating normal heart tissue using standards methods for determining protein levels such as those taught herein and known in the art. Decreased levels of intracellular cTnI and cTnT, such as those indicative of an injured or diseased heart, are determined as a decrease in the levels of these proteins relative to an established normal level. By way of example, a decrease of at least 50% in the level of cTnI and/or cTnT in heart tissue being tested for damage, relative to that of healthy heart tissue (normal control), serves as a positive indicator that the heart tissue being tested is damaged and a patient from whom the damaged tissue was removed would benefit from therapeutic intervention such as that taught herein. In a more particular example, a decrease of at least 75% in the level of cTnT in heart tissue being tested for damage, relative to that of healthy heart tissue (normal control), serves as a positive indicator that the heart tissue being tested is damaged and a patient from whom the damaged tissue was removed would benefit from therapeutic intervention such as that taught herein.

A skilled practitioner would also be aware of the large body of scientific literature pertaining to the activity and levels of intracellular cTnI and cTnT in normal and diseased heart tissue. Examples of references that pertain to intracellular cTnI and cTnT in normal and diseased heart tissue include: Latif et al. (2007, J Heart Lung Transplant 26:230-235); Birks et al. (2005, Circulation 112(9 Suppl):I57-4); Day et al. (2006, Ann NY Acad Sci 1080:437-450); Van-Buren et al. (2005, Heart Fail Rev 10:199-209); de Jonge et al. (2005, Int J Cardiol 98:465-470); Wen et at (2008, J Biol Chem April 22, Epub ahead of print); Li et al. (2008, Biochem Biophys Res Commun 369:88-99); Robinson et al. (2007, Circ Res 101:1266-1273); Solzin et al. (2007, Biophys J 93:3917-3931); (Chen et al. (2007, Cardiovase Toxicol 7:114-121); Solaro et al. (2007, Circ Res 101:114-115); Kubo et al. (2007, J Am Coll Cardio 49:2419-2426); Day et al. (2007, J Mol Med 85:911-921): Milting et al. (2006, Mol Call Cardiol 41:441-450); the entire contents of each of which is incorporated herein by reference.

In another embodiment of the invention, an increase in intracellular cTnI and cTnT levels, as determined by assaying levels of the proteins before and during (or after) a therapeutic regimen, demonstrates the therapeutic efficacy of the regimen and provides evidence that the regimen is promoting restoration of normal heart function. Indeed, an increase in intracellular cTnI and cTnT levels may be used as a surrogate endpoint (i.e. a biomarker intended to substitute for a clinical endpoint) for improved heart function. If, however, intracellular cTnI and cTnT levels remain at a reduced level or are further reduced after therapeutic intervention, a skilled practitioner would reconsider the merit of the regimen with respect to the patient being treated and alter or potentially truncate the therapeutic regimen.

As used herein, "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment, "treating" or "treatment" refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both.

Invasive Procedures for Isolating Tissue

Myocardial biopsy is a common procedure in which heart tissue is obtained from the heart through a catheter, during thoracotomy, or during open chest surgery. It is commonly used to diagnose the etiology of heart failure. The heart tissue is analyzed both histologically and biochemically. The results of these tests are useful in diagnosing the cause of the heart failure. For review of myocardial biopsy in the clinical setting see Veinot (2002, Can J Cardiol. 18(3):287-96), the entire disclosure of which is incorporated herein by reference.

The results of the myocardial biopsy may indicate that heart failure is the result of such causes as scleroderma, viral myocarditis, drug toxicity or any number of causes of heart failure. This diagnosis will dictate what, if any, therapeutic intervention may be useful and should be employed.

Myocardial biopsy (or cardiac biopsy) is an invasive procedure, wherein a bioptome (a small catheter with a grasping device on the end), for example, may be used to obtain a small piece of heart muscle tissue that can be analyzed. Myocardial biopsy may be used to evaluate heart transplant rejection and to diagnose myocarditis (inflammation of the heart).

Although a skilled practitioner would be aware of the basic protocol for myocardial biopsy using a catheter, it essentially involves the following: a local anesthetic is used to numb part of the neck or groin of a patient; a practitioner inserts a plastic introducer sheath (a short) hollow tube through which the catheter is placed) into a blood vessel in the numbed region; a bioptome is inserted through the sheath and threaded to the right ventricle of the patient; and samples are collected from the heart using the grasping device of the bioptome. During the procedure, an x-ray camera is generally used to position the bioptome properly. Samples are about the size of the head of a pin. When a sufficient number of samples have been collected, the catheter is removed and localized bleeding is controlled by firm pressure. Patients may be awake and conscious during the procedure.

Certain proteins have routinely been measured in the blood stream following a myocardial event to predict and diagnose if and the extent to which the myocardium has been damaged. These proteins include, but are not limited to, creatine kinase and troponin. Detecting specific sub-types of these and other proteins in the blood stream is diagnostic of release of the proteins from the myocardium and thus damage. Detection of these indicator proteins in the sera is used routinely in the acute setting where a cardiac event is suspected and have proven useful in determining the best treatment for the patient. While useful in the acute setting, cardiac protein levels in the blood stream have no value in diagnosing or predicting heart failure more than a few days after a cardiac event, nor do they have any value in determining the etiology of heart disease or proper treatment course. As cardiac protein Levels are not elevated in the blood except for immediately following a cardiac event, measurement of these proteins in the blood stream reveals little regarding the state of the myocardium.

In contrast, the present invention describes the use of myocardial biopsy to predict which patients may be responsive to a cardioprotective, cardiorestorative and other heart failure therapy. Predicting which patient will respond to these therapies will improve treatment by helping to ensure that the correct patients receive specific therapies and, significantly, limit the number of patients that receive therapies that will have little value and thus only expose them to the risk of potentially serious side effects. Additionally, myocardial biopsy and determination of certain protein content may demonstrate which patients are responding to certain therapies and with whom treatment should be continued.

The data presented herein show that, as predicted, immediately following cardiac challenge certain proteins, including creatine kinase and troponin can be detected in the blood stream. The data also demonstrate that one can measure a stable decrease in myocardial proteins from samples of myocardium taken long after the cardiac proteins in the blood stream have returned to normal low levels. These data also show that treatment of failing hearts with neuregulin can prevent the decline and restore the cardiac protein content of the diseased heart. This restoration correlates with improved survival and cardiac physiology.

Moreover, these data demonstrate that neuregulin can restore the troponin content of the myocardium following insult. Troponin is a key protein essential for the contractile properties of the heart. Restoration of the troponin content is thus important for restoration of normal cardiac physiology. The use of myocardial troponin content measurement in a myocardial biopsy to determine if reduced troponin myocardial content is a component of the reduced cardiac function will help predict which patients may respond to a cardiorestorative therapy such as administration of a neuregulin. Additionally, myocardial troponin content measurement may be used as an assay for determining which patients are responding to a cardiorestorative therapy such as a neuregulin. Knowing when patients are responding favorably to the therapy will help predict if and when such patients should be treated again, observed or removed from therapy. Myocardial troponin content measurement may be used to optimize dosing for individual patients that are being treated for heart disease with a cardiorestorative treatment. Similarly, in a chronic disease state in which continuous decline of cardiac troponin levels occur, maintenance of myocardial troponin levels may indicate success of a cardioprotective therapy such as a neuregulin the presence of ongoing disease. In this manner myocardial troponin levels may similarly be used to predict response to therapy and optimization of dosing.

Dosing for GGF2 or EGFL domains of neuregulin, for example, can be initiated at about 100 mg/kg and dosing thereof titrated to higher levels based on patient response, including an assessment of intracellular levels of cTnI and cTnT in cardiac tissue of the patient.

Once isolated, intracellular levels of cTnI and cTnT in cardiac tissue can be determined by methods described in the Examples presented herein and known in the art. Cellular lysates of isolated cardiac tissue or precipitates derived therefrom may, for example, be analyzed using a variety of techniques including, but not limited to, immunoblot analysis, enzyme-linked immunosorbent assay (ELISA), and mass spectrometry. Indeed, an ELISA protocol has been developed to detect cardiac-specific troponin T that utilizes a high-affinity, cardiac-specific antibody (M11.7). The detection limit of this assay is lower than that of first generation ELISA protocols that used the cross-reacting antibody 1B10 (0.0123 µg/L versus 0.04 µg/L respectively).

Methods for Detecting Troponin I and T Levels In Vivo

Technological advances in the field of molecular imaging have made possible noninvasive, high-resolution in vivo imaging techniques that enable clinicians to diagnose and evaluate therapeutic efficacy on a molecular and cellular level. The term molecular imaging is, indeed, "broadly defined as the in vivo characterization and measurement of biological processes at the cellular and molecular level". See Weissleder et al, (Radiology 219:316-333, 2001), which is incorporated herein in its entirety. Nuclear imaging, for example, which includes positron emission tomography (PET), micro-PET, single photon emission computed tomographic (SPECT), and planar imaging, generally involves visualizing an endogenous or expressed protein using specific radiopharmaceuticals as detection probes. PET, for example, is capable of producing a three-dimensional image or map of functional processes in the body which facilitates real time analyses of cellular components and molecular interactions within cells. PET is used as both a medical and a research tool. With respect to medical applications, it is used extensively in clinical oncology to image tumors and detect metastases and in clinical diagnosis of a variety of brain diseases, especially those associated with dementia. The ability to perform repeated PET analyses on a patient enables a skilled practitioner to compare results over time so as to evaluate, for example, disease progression or efficacy of a selected treatment protocol. PET has also been used as a research tool to map normal human brain and heart function.

Alternative methods of scanning include x-ray computed tomography (CT), magnetic resonance imaging (MRI), functional magnetic resonance imaging (fMRI), and ultrasound. Imaging scans such as CT and MRI are well suited to visualize organic anatomic changes in the body, whereas, as indicated above, PET scanners, like SPECT and fMRI, have the resolution to detect changes on a molecular level, even in advance of changes evident on the anatomic level. Imaging scans such as PET achieve this end by using radiolabeled molecular probes that exhibit different rates of uptake, depending on the type and function of the tissue of interest. Alterations in regional blood flow in various anatomic structures can also be visualized and quantified with a PET scan. Some of the above scanning techniques can be used in combination, depending on compatibility of radioisotopes utilized, so as to provide more comprehensive information that improves the accuracy of the clinical assessment. This is discussed herein below with respect to SPECT imaging.

As indicated above, nuclear imaging techniques such as PET, micro-PET, SPECT, and planar imaging, are directed to visualizing an endogenous or expressed protein using specific radiopharmaceuticals as detection probes. Imaging marker genes that encode intracellular enzymes and imaging marker genes that encode cell surface proteins or receptors have been used successfully in a variety of experimental systems to image specific molecules in vivo. The activity of an intracellular enzyme may also be assessed by labeling by-products indicative of the level and/or activity of a particular intracellular enzyme. PET and microPET, for example, use positron-labeled molecules to image processes involved in metabolism, cellular communication, and gene expression. Molecular imaging technologies are described in Kim (Korean J Radiology 4:201-210, 2003), which is incorporated herein by reference in its entirety.

Radionuclides used in PET scanning are typically isotopes with short half lives such as $^{11}C$ (~20 min), $^{13}N$ (~10 min), $^{15}O$ (~2 min), and $^{18}F$ (~110 min). These radionuclides are incorporated into compounds normally used by the body such as glucose, water or ammonia and then injected into the body to trace where they become distributed. Such labeled compounds are known as radiotracers. The short half-life of these radiotracers restricts clinical PET primarily to the use of tracers labeled with $^{18}F$, which has a half life of 110 minutes and can be transported a reasonable distance before use, or to $^{82}Rb$, which can be created in a portable generator and is used for myocardial perfusion studies.

SPECT is an example of a nuclear medicine tomographic imaging technique that uses gamma rays. It is very similar to conventional nuclear medicine planar imaging using a gamma camera. Unlike planar imaging, however, SPECT can provide true 3D information. This information is typically presented as cross-sectional slices through the patient, but can be modified with regard to presentation as required. The image obtained by a gamma camera image is a 2-dimensional view of 3-dimensional distribution of a radionuclide. Because SPECT acquisition is very similar to planar gamma camera imaging, the same radiopharmaceuticals may be used for either protocol. If a patient is examined using an alternative type of nuclear medicine scan, for example, but the images are non-diagnostic, it may be possible to perform a subsequent imaging scan using SPECT by reconfiguring the camera for SPECT image acquisition while the patient remains on the table or moving the patient to a SPECT instrument.

SPECT can also be used for cardiac gated acquisitions. To obtain differential information about the heart in various parts of its cycle, gated myocardial SPECT can be used to obtain quantitative information about myocardial perfusion, thickness, and contractility of the myocardium during various parts of the cardiac cycle, it is also used to facilitate calculation of left ventricular ejection fraction, stroke volume, and cardiac output.

Myocardial perfusion imaging (MPI) is an example of functional cardiac imaging, which is used for the diagnosis of ischemic heart disease. It is based on the principle that impaired or diseased myocardium receives less blood flow than normal myocardium under conditions of stress. In brief, a cardiac specific radiopharmaceutical is administered, for example, $^{99m}$Tc-tetrofosmin (Myoview™, GE healthcare) or $^{99m}$Tc-sestamibi (Cardiolite®, Bristol-Myers Squibb), after which administration the heart rate is raised to induce myocardial stress. In accordance with standard practice, enhanced heart rate is typically either exercise induced or pharmacologically induced with adenosine, dobutamine or dipyridamole. SPECT imaging performed after induction of stress reveals the distribution of the radiopharmaceutical, and therefore the relative blood flow to the different regions of the myocardium. Diagnosis is made by comparing stress images to a subsequent set of images obtained at rest.

In that troponin is a structural component of the cytoskeleton and an enzyme, molecular imaging techniques are envisioned to measure intracellular cTnI and cTnT levels in vivo.

Indeed, cardiac troponin T is present in myocytes at high concentrations, both in cytosolic and structurally-bound protein pools. The cytosolic pool amounts to 6%, whereas the amount in myofibrils corresponds to 94% of the total troponin T mass in the cardiomyocyte. In view of the high levels normally present in myocytes, labeling of either or both pools of troponin T will generate sufficient signal to be visualized with a reasonable degree of accuracy and resolution.

One potential approach envisioned for visualizing troponin complexes in cardiac tissue in vivo takes advantage of the calcium ($Ca^{2+}$) binding properties of this complex. It is known that contraction is initiated by $Ca^{2+}$ binding to troponin (Tn) in striated muscle, and more particularly by the $Ca^{2+}$-binding subunit of Tn (TnC), which leads to myosin binding to actin, force generation and shortening. The level of force is regulated by the availability of myosin binding sites on the thin filament, which is controlled by the position of tropomyosin (Tm) on the surface of actin. The inhibitory subunit of Tn (TnI) binds to actin in the absence of $Ca^{2+}$, anchoring Tm so as to inhibit myosin binding. When $Ca^{2+}$ binds to TnC, it induces strong TnI-TnC interactions and weakens the TnI-actin interactions, resulting in increased mobility of Tm and exposure of strong myosin binding sites on actin. In addition, myosin binding to actin leads, to crossbridge formation, which is thought to further displace Tm from blocking positions and is necessary for maximal activation of thin filaments in skeletal muscle.

In view of the above properties, a skilled practitioner would envision utilizing a $Ca^{2+}$ radionuclide to visualize cytoskeletal components and, more particularly, troponin levels in cardiac tissue in vivo. Alternatively, small molecules that specifically recognize either cTnI or cTnT may be labeled with radionuclides and administered to patients to visualize intracellular levels of these proteins. A skilled practitioner could envision a variety of labeled probes of utility in the present method, including ligands, antibodies, and substrates of cTnI or cTnT and/or proteins that interact with cTnI or cTnT.

Radiopharmaceuticals such as those described in U.S. Pat. No. 5,324,502 may also be used to advantage in the present method for imaging myocardial tissues. As described in U.S. Pat. No. 5,324,502, such radiopharmaceuticals are prepared by forming lipophilic, cationic complexes of radioactive metal ions with metal chelating ligands comprising the Schiff base adducts of triamines and tetraamines with optionally substituted salicylaldehydes. These lipophilic, cationic, radioactive complexes exhibit high uptake and retention in myocardial tissues. Preferred gallium-68(III) complexes in accordance with this invention can be used to image the heart using positron emission tomography. In an aspect of the present invention, such radiopharmaceuticals may be used as a means for targeting uptake of agents that bind to the troponins to cardiac tissue.

Pharmaceutical Compositions

The present invention also provides pharmaceutical compositions. Such compositions comprise a therapeutically effective amount of an agent, and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions contain a therapeutically effective amount of the compound, preferably in purified form, together with a suitable amount of carrier so as to provide a form for proper administration to a subject. The formulation should suit the mode of administration.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of a heart damage can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu (1987) J. Biol. Chem. 262:4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers.

In another embodiment, the compound or agent can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or agent can be delivered in a controlled release system. In one embodiment, a pump may be used (see Langer, supra; Sefton (1987) CRC Crit. Ref. Biomed, Eng. 14:201; Buchwald et al. (1980) Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., damaged heart, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, particular methods and materials are now described. All publications mentioned herein are incorporated herein by reference to disclose and describe the methods and/or materials in connection with which the publications are cited.

Example I

The present inventors have previously reported that GGF2, a recombinant neuregulin-1, improves survival and cardiac function in doxorubicin-treated mice. As described herein, the present inventors have investigated whether GGF2 prevents doxorubicin-induced cardiac myofibril loss in vivo and in cardiomyocytes in vitro. The results presented heroin have led to the novel discovery that the intracellular expression levels of particular cardiac proteins are useful indicators of normal heart function. More specifically, the present inventors have discovered that changes in the intracellular levels of cardiac troponin I (cTnI) and cardiac troponin T (cTnT) in intact cardiac tissue can be used as indicators of cardiac damage. In a particular aspect of the invention, a decrease in intracellular cTnI and cTnT levels in intact cardiac tissue has been shown to be a useful diagnostic marker to identify patients at risk for or experiencing cardiac damage. Such patients are then selected for appropriate preventative or therapeutic intervention as described herein. Determination of intracellular cTnI and cTnT levels in intact cardiac tissue may also be used to advantage to evaluate the efficacy of ongoing therapeutic intervention, since restoration of normal intracellular cTnI and cTnT levels would serve as a positive indicator that the therapy was improving heart function or restorative of normal heart function.

Materials and Methods

Materials

C57BL/6 mice and Wistar rats were obtained from Charles River Laboratories. Doxorubicin was obtained from Bedford laboratories. Glial growth factor 2 was a gift from Acorda Therapeutics, Inc. MG132, cycloheximide and actinomycin were obtained from Sigma. LY294002 and PD 98059 were from Cell Signalling Technology. Antibodies were ordered from the following vendors: Troponin I, GATA4 and Nkx2.5 were from Santa Cruz Biotechnology; α-sarcomeric actin, troponin T, troponin C, tropomyosin and cardiac troponin T were from Abcam; Desmin and α-actinin were from Sigma and cardiac troponin I were from GeneTex. MEM, Hank's solution and fetal bovine serum were obtained from Invitrogen. All other reagents for cell culture were obtained from Sigma.

Animal Models

Eight to ten week old C57BL/6 male mice were used for analyses wherein heart samples were isolated. A subacute doxorubicin cardiotoxicity model was used for this study. Mice were treated with a single dose of doxorubicin (20 mg/kg, i.p.). Twenty-four hours before, on the day, and every day after doxorubicin treatment, mice were treated with either GGF2 (0.75 mg/kg, s.c.) or placebo (formulation buffer for GGF2). Mice were sacrificed 4.5 days after doxorubicin treatment. Heart samples (n=3-4 per group) were collected and snap-frozen in liquid nitrogen.

With respect to those analyses wherein cardiac function was measured (as detailed below), three-month old C57BL/6 mice were treated with a single dose of doxorubicin (20 mg/kg, i.p.). Glial growth factor 2 (GGF2-Dox, 0.75 mg/kg, s.c., n=74) or placebo (the buffer used to dissolve GGF2, placebo-Dox, n=73) was injected into mice one day before and once daily following doxorubicin treatment. Mice without doxorubicin treatment were used as controls (m=20). Cardiac function was assessed by direct left ventricular (LV) catheterization four days and two weeks after doxorubicin treatment. Two-week survival was analyzed by the Kaplan-Meier methods.

Neonatal Cardiac Myocyte Culture

Neonatal cardiac myocytes were dissociated as described previously (Okoshi et al. Journal of Cardiac Failure. 2004; 10:511-518). In brief, ventricles from day 0-day 3 Wistar rats were dissociated in trypsin and Dnase II. Cells were washed and pre-plated in 100 mm dishes in MEM containing 5% fetal bovine serum. After 30 minutes, the myocytes were suspended in the same medium containing 0.1 mmol/L bromodeoxyuridine and then plated at the density of 500-1000 cells/mm$^2$ in 100 mm culture dishes. Forty-eight hours after dissociation, the medium was changed to serum-free MEM containing 0.1% BSA and cultured overnight before stimulation.

NRG1 Improved Survival and Cardiac Function in Doxorubicin-Treated Mice.

Figure 1B:
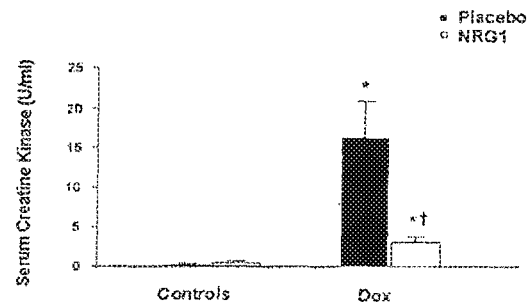

The present results reveal that two-weeks after doxorubicin treatment, survival in doxorubicin treated mice as significantly decreased compared with non-treated control mice. Concomitant treatment with NRG1 (Dox-NRG1), however, significantly improved survival in doxorubicin-injured mice compared to placebo-treated mice (Dox-Placebo) (FIG. 1A). Cardiac function was further assessed five days after doxorubicin injection, at which point, survival started to decline in doxorubicin-treated mice. As shown in Table 1, the body weight (BW), heart weight (HW) and left ventricular weight (LVW) were significantly decreased in both Dox-Placebo and Dox-NRG1 mice compared with control (untreated) mice. HW and LVW normalized by tibia length (HW/TL and LVW/TL) were significantly decreased in Dox-Placebo mice compared to control mice. These indices were not, however, different between Dox-NRG1 and control mice. LV systolic pressure (LVSP), cardiac output and dP/dt min were significantly decreased in Dox-Placebo mice compared with controls. In contrast, these indicators of heart function were not significantly different between Dox-NRG1 mice and control mice, indicating an improvement of cardiac, systolic function in NRG1 (Dox-NRG1) treated mice compared with Placebo treated mice (Dox-Placebo). Serum creatine kinase (CK) levels, an index of cardiac injury, were also assessed to provide an additional read-out of heart function. As shown in FIG. 1B, the CK level was significantly increased in both Dox-Placebo and Dox-NRG1 mice compared to control mice. The CK level was significantly lower in Dox-NRG1 mice, however, as compared with Dox-Placebo mice. These results demonstrated that NRG-1 treatment significantly improved survival and cardiac systolic function in doxorubicin-injured mice.

TABLE 1

Hemodynamic measurements in Dox + Placebo and Dox + NRG1 treated C57BL/6 mice.

| Group | Control (n = 8) | Dox + Placebo (n = 9) | Dox + NRG1 (n = 8) |
| --- | --- | --- | --- |
| BW (g) | 25 ± 0.4 | 20 ± 0.4† | 21 ± 0.9† |
| TL (mm) | 16.7 ± 0.6 | 16.3 ± 0.2 | 16.0 ± 0.0 |
| HW (mg) | 110 ± 3 | 83 ± 3† | 89 ± 3† |
| LVW (mg) | 88 ± 2 | 70 ± 1† | 75 ± 3† |
| HW/BW (mg/g) | 4.5 ± 0.1 | 4.1 ± 0.1† | 4.2 ± 0.1 |
| LVW/BW (mg/g) | 3.6 ± 0.1 | 3.5 ± 0.1 | 3.6 ± 0.1 |
| HW/TL (mg/mm) | 6.6 ± 0.3 | 5.1 ± 0.1† | 5.7 ± 0.2 |
| LVW/TL (mg/mm) | 5.4 ± 0.2 | 4.4 ± 0.1† | 4.8 ± 0.2 |
| LVSP (mmHg) | 100 ± 3 | 84 ± 2* | 91 ± 4 |
| LVEDP (mmHg) | 3.9 ± 1.4 | 3.6 ± 0.9 | 4.1 ± 1.1 |
| dP/dt max (mmHg/sec) | 10914 ± 856 | 7067 ± 884 | 9709 ± 1181 |
| dP/dt min (mmHg/sec) | 7859 ± 510 | 5021 ± 602* | 7211 ± 725 |
| EF (%) | 27 ± 2 | 17 ± 2† | 20 ± 2* |
| Cardiac Output (ul/min) | 3276 ± 469 | 118 ± 203† | 2052 ± 423 |
| HR (beat/min) | 512 ± 40 | 407 ± 39 | 540 ± 45 |

*p < 0.05;
†p < 0.01 vs. Control.

NRG1 Alleviated Doxorubicin-Induced Down-Regulation of cTnI and cTnT in the Heart In Vivo.

Figure 1C:
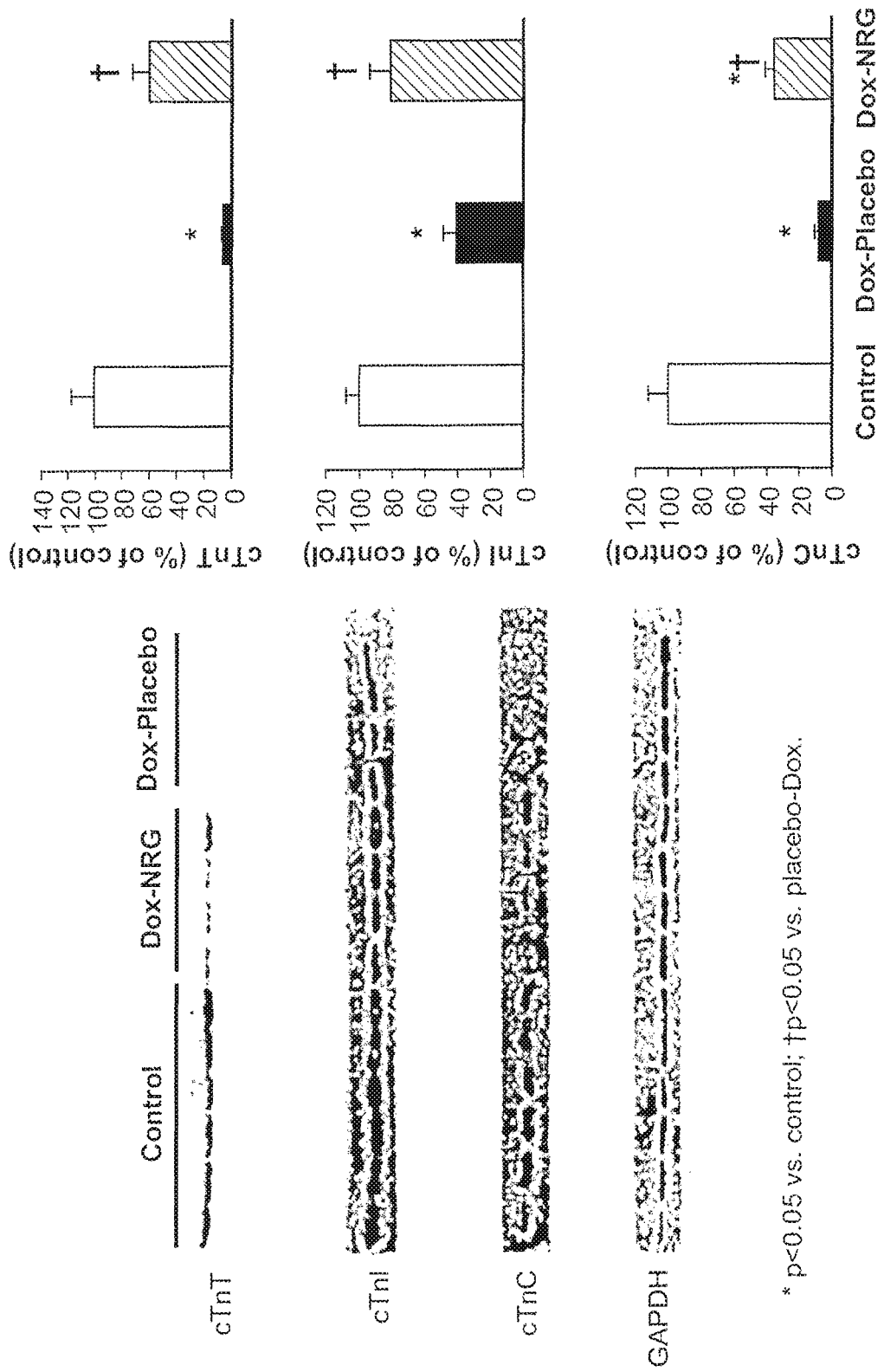

One of the mechanisms of doxorubicin-induced cardiotoxicity is loss of cardiac myofibrils. As described herein, the present inventors investigated whether NRG1 injection in vivo inhibited doxorubicin-induced myofibril loss. Results presented herein demonstrate that the levels of cardiac structural proteins, α-sarcomeric actin, α-actinin, troponin T (TnT), troponin I (TnI), troponin C (TnC) and tropomyosin were significantly decreased in doxorubicin-treated hearts. NRG1 injection in vivo significantly increased the protein levels of cTnI, cTnT and cTnC in doxorubicin-injured hearts (FIG. 1C), but had no effects on the protein levels of α-sarcomeric actin, α-actinin and tropomyosin.

NRG1 Abolished Doxorubicin-Induced Down-Regulation of cTnI and cTnT Proteins in Cardiomyocytes In Vitro.

Figure 2A:
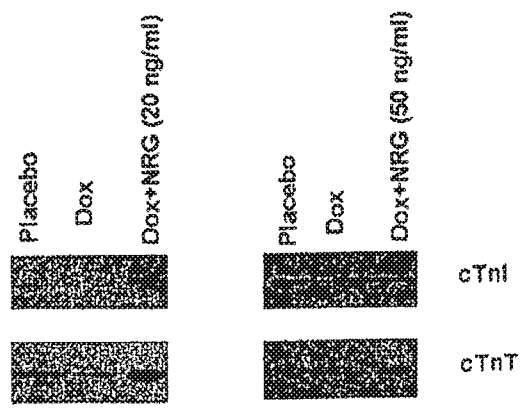
FIGS. 2A-D show immunoblots probed to detect the indicated proteins.
Figure 2B:
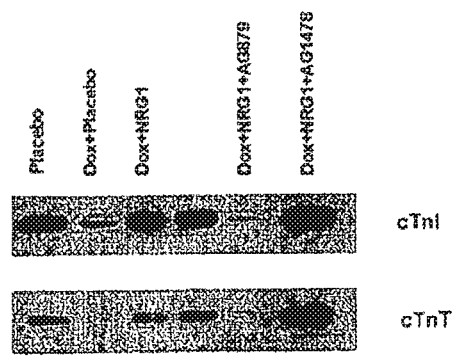
Figure 2C:
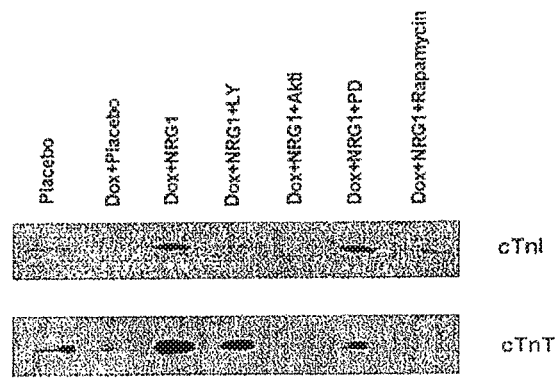

To further study the mechanism of how NRG1 inhibited doxorubicin-induced down-regulation of cTnI and cTnT, the present inventors conducted in vitro studies using neonatal rat cardiomyocyte culture (NRCM). As shown in FIG. 2A, doxorubicin significantly reduced the protein levels of cTnI and cTnT in NRCM; the presence of NRG-1, however, maintained the levels of these proteins in doxorubicin-treated cardiomyocytes. These results further demonstrated that these effects of NRG1 were blocked by inhibitors for erbB2, PI3K, Akt, mTOR or ERK (FIGS. 2B and 2C), but were not blocked by inhibitors for erbB4 (FIG. 2B), p38 or PKC. The instant results also showed that the preventative and/or restorative effects of NRG1 were blocked by cycloheximide, a protein translation inhibitor (FIG. 2D), but not by actinomycin D, a transcription inhibitor. Doxorubicin-induced down-regulation of cTnI and cTnT was abolished by Z-VAD, a pan-caspase inhibitor, and MG132, a proteasome inhibitor (FIG. 2D), but not by bafilomycin A1, a lysosome inhibitor.

NRG1 Inhibited Doxorubicin-Induced Caspase and Proteasome Degradation of cTnI and cTnT in Cardiomyocytes In Vitro.

The maintenance of the level of a protein in the cell is a dynamic process. It depends on the rate of synthesis and degradation of a protein. The present inventors explored the mechanism whereby doxorubicin decreased the protein levels of cTnI and cTnT to determine if this effect is caused by increasing their degradation and/or by decreasing their synthesis and whether NRG1 blocked any of these effects of doxorubicin.

Figure 3A:
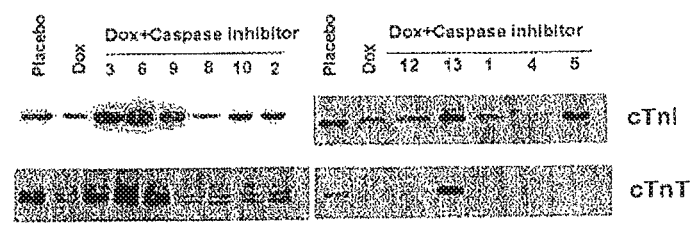
FIGS. 3A-3D show immunoblots (A, C, D), and histograms (B).
Figure 3B:
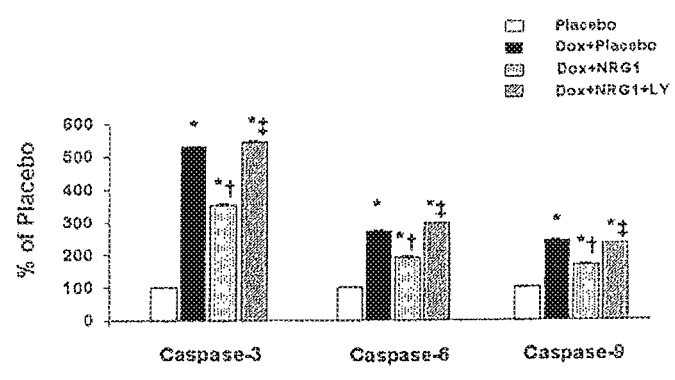
Figure 3B:
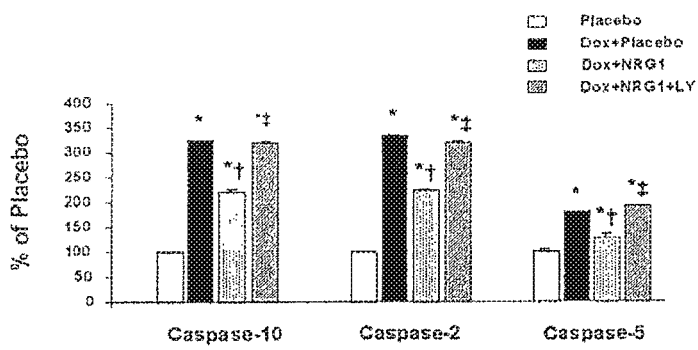
Figure 3C:
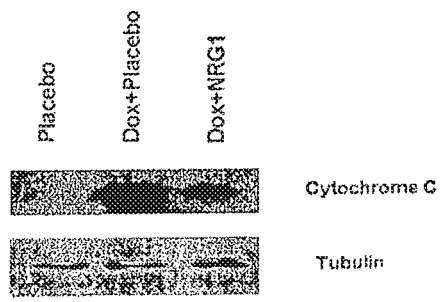

To investigate whether NRG1 inhibited doxorubicin-induced caspase degradation of cTnI and cTnT, the present inventors first identified the specific caspases that were responsible for doxorubicin-induced degradation of cTnI and cTnT. Cardiomyocytes wore treated with doxorubicin in the presence of a specific caspase inhibitor. As shown in FIG. 3A, inhibitors for caspase-3, caspase-6 or caspase-9 (intrinsic pathway) blocked doxorubicin-induced down-regulation of both cTnI and cTnT. In addition, down-regulation of cTnI was blocked by inhibitors for caspase-10 (extrinsic pathway), caspase-2, caspase-13 caspase-5. On the other hand, the down-regulation of cTnT was also blocked by caspase-2 and caspase-13. The present inventors then tested whether doxorubicin activated and whether NRG1 inhibited the activation of these caspases. An in vitro caspase activation assay revealed that doxorubicin significantly increased the activation of caspase 3, 6 and 9 as well as caspase-10, 2, and 5. NRG1 treatment of cardiomyocytes significantly inhibited doxorubicin-induced activation of these caspases (FIG. 3B). PI3K inhibitor LY294002 abolished these effects of NRG1. The present inventors further demonstrated that doxorubicin induced increasing of cytochrome c release to the cytosol in NRCM. NRG1 treatment, however, inhibited this effect of doxorubicin (FIG. 3C). This result, in combination with the findings of caspase-3, 6 and 9 activations, suggested that doxorubicin increased mitochondrial outer membrane permeabilization, which may be responsible for the activation of caspase-3, 6 and 9, and NRG1 blocked these effects of doxorubicin. These results demonstrated that NRG-1 inhibited doxorubicin-induced activation of both intrinsic and extrinsic caspase activation, which were responsible, at least in part, for the degradation of cTnI and cTnT.

Figure 2D:
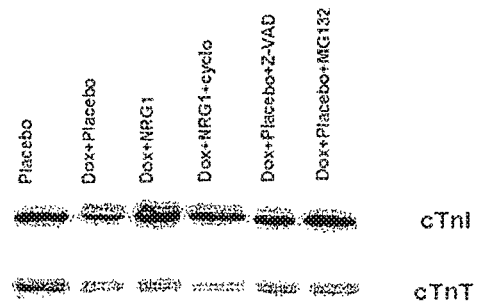
Figure 3D:
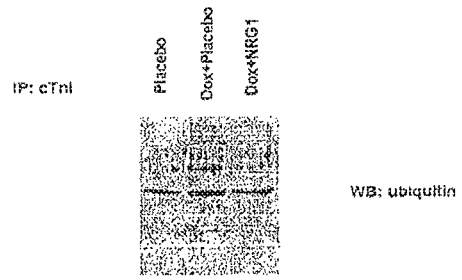

The present inventors further demonstrated that doxorubicin-induced down-regulation of cTnI was blocked by MG132 (FIG. 2D). In short, the present inventors asked whether doxorubicin increased proteasome degradation of cTnI and whether NRG1 blocked this effect. As shown in FIG. 3D, doxorubicin increased the ubiquitinylation of cTnI; NRG1 treatment abolished this effect of doxorubicin. This result demonstrated that NRG1 decreased doxorubicin-induced proteasome degradation of cTnI.

NRG1 Alleviated Doxorubicin-Induced Decrease in Synthesis of cTnI and cTnT in Cardiomyocytes In Vitro.

Figure 4A:
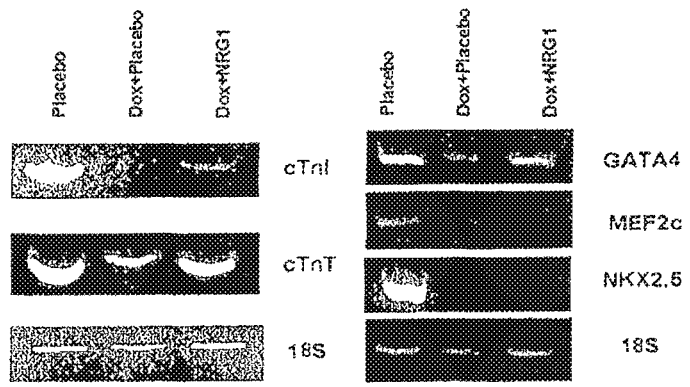
FIGS. 4A-4B show ethidium bromide stained agarose gels (A) and immunoblots (B).

To further test whether doxorubicin decreased the transcription of cTnI and cTnT and whether NRG1 reversed this effect of doxorubicin, the mRNA levels of these proteins in Dox-Placebo and Dox-NRG1 treated cardiomyocytes were measured. As shown in FIG. 4A, doxorubicin decreased the mRNA of both cTnI and cTnT. On the other hand, NRG1 maintained the mRNA level of cTnI and cTnT in doxorubicin-treated cardiomyocytes. In addition, NRG1 maintained the mRNA level of GATA4 and slightly increased the mRNA level of MEF2c and Nkx2.5 (FIG. 4A), which are transcriptional factors important for cardiac specific gene transcription.

Figure 4B:
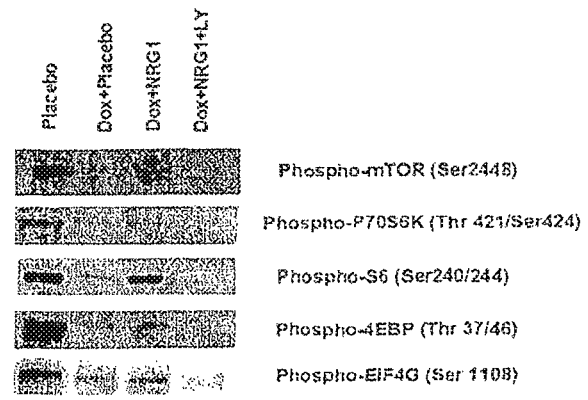

The present results showed that NRG-1's effects on cTnI and cTnT were blocked by cycloheximide (FIG. 2D), suggesting that NRG1 increased the translation of these proteins. We assessed the activation of several translation machineries and related signaling pathways in Dox-Placebo and Dox-NRG1 treated cardiomyocytes. As shown in FIG. 4B, 48 hours after the treatment, the phosphorylation levels of mTOR (Ser 2448), P70S6K (Thr42/Ser424), S6(Ser240/244) and eIF4G (Ser1108) were decreased in Dox-Placebo, but were maintained in Dox-NRG1 treated cardiomyocytes. LY294002 blocked these effects of NRG-1. These results suggest that NRG, via PI3K, maintained the activation of protein translational machineries in doxorubicin-treated cardiomyocytes, which may be responsible for maintaining the protein levels of cTnI and cTnT.

These results demonstrated that NRG1 alleviated doxorubicin-induced down-regulation of cTnI and cTnT via multiple mechanisms, which include inhibition of the activation of intrinsic and extrinsic caspases, as well as inflammatory activated caspases, inhibition of the ubiquitinylation of cTnI, and an increase in transcription and the activation of translation signaling and machineries. These results also suggested that PI3K played a major role for NRG1 in maintaining cTnI and cTnT levels in cardiomyocytes.

Figure 5A:
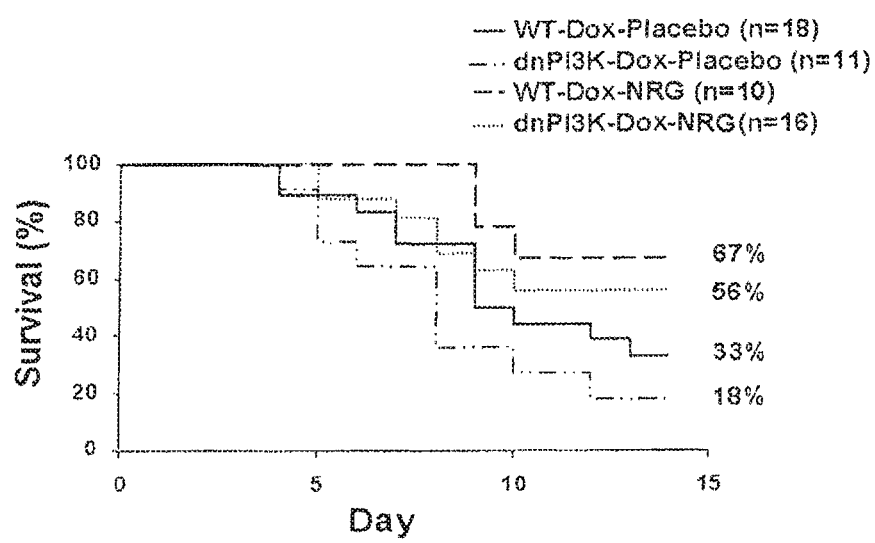
FIGS. 5A-5C show a survival graph (A), histograms (B), and an immunoblot (C).

To further investigate the role of PI3K in mediating NRG1's cardiac protective effects in vivo, the present inventors used transgenic mice with cardiac myocyte-specific overexpression of a dominant negative PI3K and treated them with doxorubicin as described above. As shown in FIG. 5A, the survival rate was decreased in dnPI3K-Dox-Placebo mice compared with WT-Dox-Placebo mice. NRG1 (WT-Dox-NRG) treatment improved survival in doxorubicin injured WT (WT-Dox-Placebo) mice (67% vs. 33%). Intriguingly, the magnitude of this improvement was greater than that observed in C57BL/6 male mice (FIG. 1A). The present results further showed that this improvement of the survival rate was dampened in doxorubicin-treated dnPI3K mice (dnPI3K-Dox-NRG: 56% vs. WT-Dox-NRG: 67%).

Figure 5B:
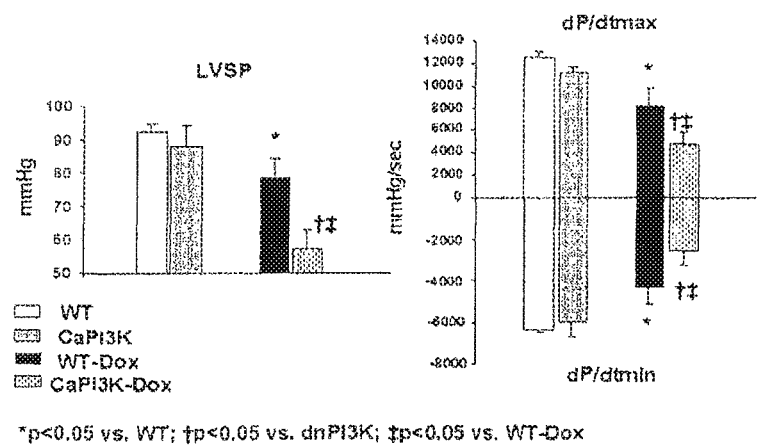

Cardiac function was also evaluated in these mice. As shown in FIG. 5B, LVSP, dP/dt max and dP/dt min, as well as cardiac output were more severely depressed in dnPI3K-Dox-Placebo mice compared with dnPI3K control than WT-Dox-Placebo mice compared with WT mice, indicating more severe cardiac dysfunction in dnPI3K-Dox-Placebo mice.

Figure 5C:
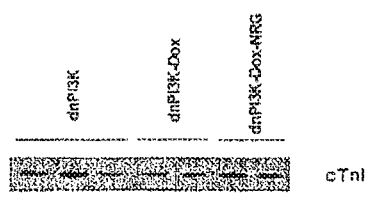

The present inventors measured cTnI and cTnT protein levels in doxorubicin-treated WT and dnPI3K mice. Without doxorubicin treatment, the protein levels of cTnI and cTnT were similar in WT and dnPI3K hearts. Two-weeks after the doxorubicin injection, a decrease in cTnI protein levels was observed in dnPI3K-Dox-Placebo treated hearts compared with non-treated dnPI3K hearts. Surprisingly, NRG1 treatment still abolished doxorubicin-induced down-regulation of cTnI in dnPI3K hearts (dnPI3K-Dox-NRG, FIG. 5C). No changes in cTnT protein levels were observed in the hearts of doxorubicin-treated mice compared to control mice at this point.

These results demonstrate that GGF2 specifically maintains TnT and TnI protein levels in doxorubicin-injured hearts. Moreover, these findings reveal that GGF2 increases survival of doxorubicin-treated mice and this is associated with an improvement in cardiac function as evident in mice treated with both doxorubicin and GGF2.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for restoring intracellular troponin content in a myocardium following insult in a subject in need thereof, comprising (i) identifying the subject in need thereof, and (ii) administering to the identified subject a compositing comprising epidermal growth factor-like (EGFL) domain of a neuregulin, wherein the subject in need thereof is identified by a method comprising: detecting intracellular levels of cardiac troponin T (cTnT) or cardiac troponin I (cTnI) in cardiac tissue of the subject, wherein a decrease in intracellular levels of either cTnT or cTnI in cardiac tissue of the subject relative to control or normal intracellular levels of either cTnT or cTnI, respectively, is indicative of heart damage of the subject.

2. The method of claim 1, wherein detecting intracellular levels of cTnT or cTnI in cardiac tissue is performed in vitro.

3. The method of claim 1, wherein detecting intracellular levels of cTnT or cTnI in cardiac tissue is performed in vivo.

4. The method of claim 1, wherein the heart damage is a result of cardiotoxicity, hypertension, valvular disorders, myocardial infarction, viral myocarditis, or scleroderma.

5. The method of claim 4, wherein the cardiotoxicity is caused by treatment with a chemotherapeutic agent or other therapeutic agent, radiation, or agents used for non-therapeutic, recreational purposes.

6. The method of claim 1, wherein the control or normal intracellular levels of either cTnT or cTnI in cardiac tissue are established by determining the intracellular levels of either cTnT or cTnI in cardiac tissue of a subject with normal heart function.

7. The method of claim 1, wherein the control or normal intracellular levels of either cTnT or cTnI in cardiac tissue are established by determining the intracellular levels of either cTnT or cTnI in cardiac tissue of the subject prior to onset of treatment capable of causing heart damage.

8. The method of claim 1, wherein the subject is a mammal.

9. The method of claim 8, wherein the mammal is a human.

10. The method of claim 1, wherein the neuregulin is glial growth factor 2 (GGF2).

11. The method of claim 1, wherein the subject has chronic heart disease.

* * * * *